(12) United States Patent
Dickensheets et al.

(10) Patent No.: US 12,072,481 B2
(45) Date of Patent: Aug. 27, 2024

(54) MICROSCOPE LENS WITH INTEGRATED WIDE-FIELD CAMERA AND BEAM SCANNING DEVICE

(71) Applicants: MONTANA STATE UNIVERSITY, Bozeman, MT (US); MEMORIAL SLOAN-KETTERING CANCER CENTER, New York, NY (US)

(72) Inventors: David Dickensheets, Bozeman, MT (US); Milind Rajadhyaksha, New York, NY (US)

(73) Assignees: MONTANA STATE UNIVERSITY, Bozeman, MT (US); MEMORIAL SLOAN-KETTERING CANCER, New York, NY (US)

( * ) Notice: Subject to any disclaimer, the term of this patent is extended or adjusted under 35 U.S.C. 154(b) by 0 days.

(21) Appl. No.: 17/717,774

(22) Filed: Apr. 11, 2022

(65) Prior Publication Data

US 2022/0244517 A1     Aug. 4, 2022

Related U.S. Application Data

(63) Continuation of application No. 16/077,352, filed as application No. PCT/US2017/017567 on Feb. 11, 2017, now Pat. No. 11,300,774.

(Continued)

(51) Int. Cl.
*G02B 21/36* (2006.01)
*A61B 5/00* (2006.01)
(Continued)

(52) U.S. Cl.
CPC .......... *G02B 21/361* (2013.01); *A61B 5/0068* (2013.01); *A61B 5/0077* (2013.01);
(Continued)

(58) Field of Classification Search
CPC .............. G02B 21/361; G02B 21/0008; G02B 21/0028; G02B 21/0036; G02B 21/02;
(Continued)

(56) References Cited

U.S. PATENT DOCUMENTS

| 5,742,419 A | 4/1998 | Dickensheets et al. |
| 5,859,814 A | 1/1999 | Kino et al. |

(Continued)

FOREIGN PATENT DOCUMENTS

WO    2014183860 A1    11/2014

OTHER PUBLICATIONS

Abeytunge et al., "Confocal microscopy with strip mosaicing for rapid imaging over large areas of excised tissue," Journal of biomedical optics, 2013, 18(6):061227, 14 pages.

(Continued)

*Primary Examiner* — Balram T Parbadia
*Assistant Examiner* — Rahman Abdur
(74) *Attorney, Agent, or Firm* — Michael Best & Friedrich LLP

(57) ABSTRACT

A device for viewing a target, the device including a housing, an objective lens positioned within the housing, where the objective lens has a first lens group including at least a first lens and a second lens group including at least a second lens, the first lens positioned closer to the target than the second lens, and a camera positioned within the objective lens between the first lens and the second lens, where the camera is configured to provide images of the target located near a focal point of the objective lens, and wherein the arrangement of the first lens, the second lens, and the camera provides for simultaneous capture of a first image of a surface of the target and a second image of a sub-surface cellular structure of the target.

14 Claims, 19 Drawing Sheets

Related U.S. Application Data

(60) Provisional application No. 62/294,705, filed on Feb. 12, 2016, provisional application No. 62/294,149, filed on Feb. 11, 2016.

(51) Int. Cl.
| | |
|---|---|
| *G02B 21/00* | (2006.01) |
| *G02B 21/02* | (2006.01) |
| *G02B 21/06* | (2006.01) |

(52) U.S. Cl.
CPC .......... *A61B 5/444* (2013.01); *G02B 21/0008* (2013.01); *G02B 21/0028* (2013.01); *G02B 21/0036* (2013.01); *G02B 21/02* (2013.01); *G02B 21/06* (2013.01); *A61B 5/0075* (2013.01)

(58) Field of Classification Search
CPC ..... G02B 21/06; A61B 5/0068; A61B 5/0077; A61B 5/444; A61B 5/0075
USPC ....................................................... 359/643
See application file for complete search history.

(56) References Cited

U.S. PATENT DOCUMENTS

| | | | |
|---|---|---|---|
| 5,880,880 | A | 3/1999 | Anderson et al. |
| 5,978,695 | A | 11/1999 | Greenwald et al. |
| 5,995,283 | A | 11/1999 | Anderson et al. |
| 6,172,786 | B1 | 1/2001 | Fujita et al. |
| 6,360,115 | B1 | 3/2002 | Greenwald et al. |
| 6,720,547 | B1 | 4/2004 | Rajadhyaksha et al. |
| 6,749,346 | B1 | 6/2004 | Dickensheets et al. |
| 7,098,871 | B1 | 8/2006 | Tegreen et al. |
| 7,110,114 | B2 | 9/2006 | Rajadhyaksha et al. |
| 7,307,774 | B1 | 12/2007 | Schnitzer et al. |
| 7,428,093 | B2 | 9/2008 | Tegreen et al. |
| 7,494,233 | B2 | 2/2009 | Himmer et al. |
| 8,237,835 | B1 | 8/2012 | Muller |
| 8,300,220 | B2 | 10/2012 | Mahadevan-Jansen et al. |
| 9,244,275 | B1 | 1/2016 | Li |
| 2007/0035855 | A1* | 2/2007 | Dickensheets ....... A61B 5/0068 359/819 |
| 2007/0188856 | A1 | 8/2007 | Macaulay |
| 2008/0030592 | A1* | 2/2008 | Border ............... H04N 5/23296 348/E5.042 |
| 2009/0162967 | A1 | 6/2009 | Cheng et al. |
| 2010/0214562 | A1* | 8/2010 | Mahadevan-Jansen ..................... A61B 5/445 356/301 |
| 2010/0321678 | A1 | 12/2010 | Koh et al. |
| 2011/0282192 | A1* | 11/2011 | Axelrod ............... A61B 5/0066 600/427 |
| 2012/0242786 | A1 | 9/2012 | Sasagawa et al. |
| 2013/0229493 | A1* | 9/2013 | Ikuta ...................... G02B 21/32 348/46 |
| 2014/0247502 | A1 | 9/2014 | Bauer et al. |
| 2014/0291492 | A1 | 10/2014 | Kusaka |
| 2016/0033681 | A1 | 2/2016 | Shih et al. |
| 2018/0358199 | A1* | 12/2018 | Kumamoto ............. H01J 37/22 |

OTHER PUBLICATIONS

Ahlgrimm-Siess et al., "Reflectance Confocal Microscopy in The Daily Practice," Seminars in Cutaneous Medicine and Surgery, 2009, 28(3):180-9.

Alarcon et al., "Impact of in vivo reflectance confocal microscopy on the number needed to treat melanoma in doubtful lesions," British Journal of Dermatology, 170(4):802-808, 2014.

Alessi et al., "Reflectance confocal microscopy as a new tool in the in vivo evaluation of desquamative gingivitis: patterns in mucous membrane pemphigoid, pemphigus vulgaris and oral lichen planus," British Journal of Dermatology, 2013, 168(2):257-264.

Anuthama et al., "Characterization of different tissue changes in normal, betel chewers, potentially malignant lesions, conditions and oral squamous cell carcinoma using reflectance confocal microscopy: Correlation with routine histopathology," Oral Oncology, 2010, 46(4):232-248.

Aquirre et al., "Two-axis MEMS Scanning Catheter for Ultrahigh Resolution Three-dimensional and En Face Imaging ," Optics Express, 2007, 15(5):2445-2453.

Argenziano et al., "Accuracy in melanoma detection: a 10-year multicenter survey," Journal of the American Academy of Dermatology, 2012, 67(1):54-9.

Arrasmith et al., "MEMS-based handheld confocal microscope for in-vivo skin imaging," Optics Express, 2010, 18(4):3805-3819.

Astner et al., "Confocal microscopy: innovative diagnostic tools for monitoring of noninvasive therapy in cutaneous malignancies," Drug Discovery Today: Disease Mechanisms, 2008, 5(1):e81-e91.

Astner et al., "RCM-assisted assessment of treatment response," Reflectance Confocal Microscopy of Cutaneous Tumors—An Atlas with Clinical, Dermoscopic and Histological Correlations, 2008, Chapter 6C, pp. 219-230.

Awan et al., "Utility of chemiluminescence (ViziLite™) in the detection of oral potentially malignant disorders and benign keratoses," J Oral Pathol med, 2011, 40(7):541-4.

Balagula et al., "The significance of crystalline/chrysalis structures in the diagnosis of melanocytic and nonmelanocytic lesions," Journal of the American Academy of Dermatology, 2012, 67(2):194.e1-194.e8.

Bassoli et al., "Reflectance confocal microscopy criteria of lichen planus-like keratosis," Journal of the European Academy of Dermatology and Venereology, 2012, 26(5):578-90.

Boreman et al., "Modulation transfer function measurement using three-and four-bar targets," Applied optics, 1995, 34(34):8050-8052.

Braga et al., "The significance of reflectance confocal microscopy in the assessment of solitary pink skin lesions," Journal of the American Academy of Dermatology, 2009, 61(2):230-241.

Braun et al., "Agreement of dermatopathologists in the evaluation of clinically difficult melanocytic lesions: how golden is the 'gold standard'?" Dermatology, 2012, 224(1):51-8.

Brocklehurst et al., "Screening programmes for the early detection and prevention of oral cancer," Cochrane Systematic Review, 201\3, Issue 11, Article No. CD004150, 34 pages.

Busam et al., "Detection of Clinically Amelanotic Malignant Melanoma and Assessmentof Its Margins by In Vivo Confocal Scanning Laser Microscopy," Arch Dermatol, 2001, 137(7):923-929.

Carlson et al., "In vivo fiber-optic confocal reflectance microscope with an injection-molded plastic miniature objective lens," Applied Optics, 2005, 44(10):1792-1797.

Chen et al., "Multimodal in vivo optical imaging, including confocal microscopy, facilitates presurgical margin mapping for clinically complex lentigo maligna melanoma," British Journal of Dermatology, 2005, 153(5):1031-6.

Chen et al., "Redefining the number needed to excise," Australasian Journal of Dermatology, 2013, 54(4):310-2.

Chinese Patent Office Action for Application No. 201780016643.7 dated Mar. 7, 2022 (19 pages, English translation Included).

Chinese Patent Office Action for Application No. 201780016643.7 dated May 11, 2021(24 pages, English translation Included).

Contaldo et al., "In vivo characterization of healthy oral mucosa by reflectance confocal microscopy: a translational research for optical biopsy," Ultrastruct Pathol, 2013, 37(2):151-158.

Cox et al., "Reappraisal of arrays of concentric annuli as super-resolving filters," J. Opt. Soc. Am., 1982, 72(9):1287-1291.

Cukras, "On the Comparison of Diagnosis and Management of Melanoma Between Dermatologist and MelalFind," JAMA Dermatol, 2012, 149(5):622-3.

Curiel-Lewandrowski et al., "Use of in vivo confocal microscopy in malignant melanoma—An aid in diagnosis and assessment of surgical, and nonsurgical therapeutic approaches," Archives of Dermatology, 2004, 140(9):1127-1132.

Dalle et al., "Tracking of second primary melanomas in vemurafenib-treated patients," JAMA dermatology, 2013, 149(4):488-90.

(56) References Cited

OTHER PUBLICATIONS

Debarbieux et al., "Perioperative confocal microscopy of the nail matrix in the management of in situ or minimally invasive subungual melanomas," British Journal of Dermatology, 2012, 167(4):828-836.

Debarbieux et al., "Reflectance confocal microscopy accurately discriminates between benign and malignant melanocytic lesions exhibiting a 'dermoscopic island'," J Eur Acad Dermatol Venereal, 2013, 27(2):e159-65.

Diaconeasa et al., "The role of confocal microscopy in the dermato-oncology practice," Journal of Medicine and Life, 2011, 4(1):63-74.

Dickensheets et al., "Wide-field imaging combined with confocal microscopy using a miniature f/5 camera integrated within a high NA objective lens," Optics Letters, Mar. 2017, 42(7):1241-1244.

Dickensheets et al., "A Micromachined Scanning Confocal Optical Microscope," Optics Letters, 1996, 21:764-766.

Dickensheets et al., "A novel miniature confocal microscope/Raman spectrometer system for biomolecular analysis on future Mars missions after Antarctic trials," Journal of Raman Spectroscopy, 2000, 31(7):633-5.

Dickensheets et al., "Dermoscopy-guided reflectance confocal microscopy of skin using high-NA objective lens with integrated wide-field color camera," Proc SPIE Int Soc Opt Eng, 2016, 9689:96890U-U6.

Dickensheets et al., "Focus Tracking in Time Domain Optical Coherence Tomography using Membrane Mirrors Operated Near Snap-Down," IEEE/LEOS International Conference on Optical MEMS and Their Applications Conference, 2006, pp. 170-171.

Dickensheets et al., "Miniature high-resolution imaging system with 3-dimensional MOEMS beam scanning for Mars exploration," SPIE, 2000, 4178:90-97.

Dickensheets et al., "Requirements of MEMS membrane mirrors for focus adjustment and aberration correction in endoscopic confocal and optical coherence tomography imaging instruments," J. Micro/Nanolith, MEMS MOEMS, 2008, 7(2):021008.

Dickensheets et al., "Silicon Micromachined Scanning Confocal Optical Microscope," IEEE J. Microelectromechanical Systems, 1998, 7(1):38-47.

Dimitrow et al., "Sensitivity and specificity of multiphoton laser tomography for in vivo and ex vivo diagnosis of malignant melanoma," J Invest Dermatol, 2009, 7:1752-8.

Dunbar et al., "Polymer deformable membrane mirrors for focus control using SU-8 2002," IEEE/LEOS International Conference on Optical MEMS, Freiburg, Germany, 2008, pp. 138-139.

Dusza et al., "Prospective Study of Sunburn and Sun Behavior Patterns During Adolescence," Pediatrics, 2012, 129(2):309-317.

Dwyer et al., "Confocal theta line-scanning microscope for imaging human tissues," Applied optics, 2007, 46(10):1843-51.

Edwards et al., "Raman spectroscopic detection of biomolecular markers from Antarctic materials: evaluation for putative Martian habitats," Spectrochimica Acta Part A: Molecular and Biomolecular Spectroscopy, 2003, 59(10):2277-90.

El Ferradi, "Objective lens for a miniature endoscopic confocal microscope," MSEE Thesis, Montana State University, 2005, 90 pages.

Ellery et al., "The role of Raman spectroscopy as an astrobiological tool in the exploration of Mars," Journal of Raman Spectroscopy, 2004, 35:441-457.

Emery et al., "Accuracy of SIAscopy for pigmented skin lesions encountered in primary care: development and validation of a new diagnostic algorithm," BMC Dermatology, 2010, 10:9, 9 pages.

European Patent Office Extended Search Report for Application No. 17750925.4 dated Feb. 4, 2020 (14 pages).

Fang et al., "Fluorescence in situ hybridization (Fish) analysis of melanocytic nevi and melanomas: sensitivity, specificity, and lack of association with sentinel node status," Int J Surg Pathol, 2012, 20(5):434-40.

Farahati et al., "Rigid confocal endoscopy for in vivo imaging of experimental oral squamous intra-epithelial lesions," J Oral Pathol Med, 2010, 39(4):318-27.

Anonymous, "Wafer Level Camera Technology—Tech Briefs," Photonics Tech Briefs, published Jul. 2009, (10 pages).

European Patent Office Action for Application No. 17750925.4 dated Sep. 1, 2022 (11 pages).

* cited by examiner

202

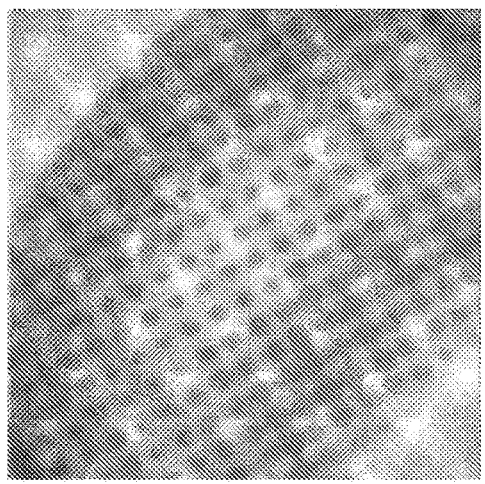
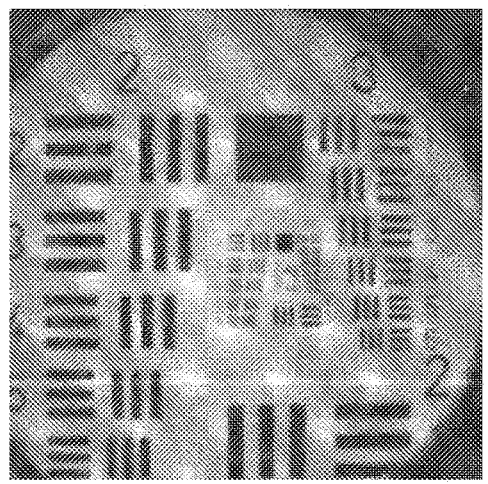
FIG. 10A
FIG. 10B

MICROSCOPE LENS WITH INTEGRATED WIDE-FIELD CAMERA AND BEAM SCANNING DEVICE

CROSS-REFERENCE TO RELATED APPLICATIONS

This application is a continuation of U.S. patent application Ser. No. 16/077,352, filed on Aug. 10, 2018, which is a national stage application of PCT/US2017/017567, filed Feb. 11, 2017, which claims priority to U.S. Provisional Application No. 62/294,149, filed on Feb. 11, 2016 and U.S. Provisional Application No. 62/294,705, filed on Feb. 12, 2016. The contents of all of these applications are incorporated herein by reference.

STATEMENT OF FEDERALLY-SPONSORED RESEARCH

This invention was made with government support under 1R21EB018507 and P30CA008748 awarded by the National Institutes of Health and under 1542210 awarded by the National Science Foundation. The government has certain rights in the invention.

BACKGROUND OF THE INVENTION

Wide-field imaging paired with reflectance confocal microscopy is advancing in clinical settings to guide non-invasive diagnosis of skin cancer. However, two separate devices are required to perform each imaging procedure.

SUMMARY OF THE INVENTION

Wide-field clinical examination followed by dermoscopy (magnification 4×-10×) is the current standard approach for guiding biopsy and pathology and diagnosis of skin lesions. However, this approach varies in specificity, depending on setting, and lesion and patient characteristics, resulting in highly variable benign-to-malignant detection rates, ranging from as low as 2-to-1 to as high as 600-to-1, which, consequently, results in millions of biopsies of benign lesions. Reflectance confocal microscopy (RCM), which noninvasively images beneath the skin surface and shows nuclear and cellular details in vivo, has been proven to increase specificity and lower the benign-to-malignant detection rate by about two times relative to that with dermoscopy alone. Wide-field clinical examination and dermoscopy combined with RCM imaging is now being implemented in clinical settings to triage lesions into those that appear benign (these patients are being spared biopsy) versus those that appear suspicious (these patients proceed to standard biopsy and pathology). The initial impact is promising in terms of reducing the need for biopsy of benign lesions.

Wide-field imaging, which shows gross morphology of a lesion, guides RCM imaging, which shows microscopic histology-level detail, which ultimately guides either non-invasive diagnosis (i.e., benign) or biopsy (i.e., suspicious). However, the wide-field imaging (clinical examination, dermoscopy) and microscopic imaging (RCM) are currently performed in series, as separate procedures with separate handheld devices. The field of view with RCM imaging is very small (less than 1 mm×1 mm) relative to that (10 mm×10 mm) for wide-field imaging. What is currently lacking, therefore, is the ability to accurately and repeatably locate the RCM field of view at small areas of suspicion within the larger wide-field image. In other words, subsurface microscopic imaging with a handheld device is being performed with limited accuracy and repeatability within the context of clinically-observed gross surface morphology, and with only subjective and thus limited means to register the RCM image to a wide-field image. This leads to increased variability and uncertainty in interpreting RCM images and in making a determination whether to biopsy. What is needed is a way to provide concurrent wide-field imaging of the skin surface, showing precisely the site undergoing RCM imaging of the subsurface cellular structure.

The challenge in providing simultaneous confocal microscopic imaging with adequately high numerical aperture (NA) and wide field imaging at lower NA in a single device is the limited field of view supported by any high-NA objective lens. The wide-field image cannot be made with the objective lens due to vignetting, and with a required NA>0.7, there is no room between the objective lens and the tissue to accommodate a beam splitter and a wide-field camera.

Embodiments of the invention provide subsurface confocal imaging with concurrent wide-field imaging, by integrating a miniature color camera inside a high NA objective lens. The camera commands a field of view of several millimeters at the surface, including the location within the lesion where RCM imaging occurs. The camera, inserted between a hyperhemisphere front lens and a back lens group of the objective, commands a field of view of 4.0 mm, with resolution better than 30 µm, while confocal optical sectioning is preserved at sharper than 2.5 µm.

The present invention generally relates to a device and method for non-invasive evaluation of a target area of interest of a subject. In particular, the present invention generally relates to handheld devices and methods that integrate wide-field dermoscopy with reflectance confocal microscopy for non-invasive simultaneous capture of wide-field color images of the skin surface and images of the sub-surface cellular structure. FIG. 1 illustrates a handheld dual-view microscope providing wide-field dermoscopy with simultaneous reflectance confocal microscopy according to an embodiment of the present invention.

A person skilled in the art will recognize that the present inventions of an integrated scanner or an integrated camera, together or separately, apply not only to reflection confocal microscopy, but any scanned-laser based imaging modality including but not limited to optical coherence tomography and optical coherence microscopy, multiphoton microscopy, second harmonic generation microscopy, photoacoustic microscopy, etc. Furthermore, approaches that do not have a scanning laser beam, such as structured light microscopy or white light optical coherence microscopy, will benefit from the integrated camera for contextualizing the microscopic field of view within the surface morphology.

In one embodiment, the invention provides a device comprising a housing, an objective lens comprising a first lens group supported by the housing and a second lens group supported by the housing, and a camera positioned between the first lens group and the second lens group, the camera configured to provide video images of a target located near a focal point of the objective lens.

In another embodiment, the invention provides a device comprising a housing, an objective lens comprising a first lens group supported by the housing and a second lens group supported by the housing; and a beam scanner and/or focusing device configured to provide scanning of a position of the focus of a beam in three-dimensions within a target space located near the focus of the objective lens.

In yet another embodiment, the invention provides a system comprising a housing, an objective lens comprising a first lens group of one or more lenses supported by the housing, a second lens group comprising zero or more lenses supported by the housing, and a third lens group comprising zero or more lenses supported by the housing, a camera positioned between the first lens group and the second lens group, the camera configured to provide video images of a target located near a focal point of the objective lens, and a beam scanner and/or focusing device positioned between the second lens group and the third lens group, the beam scanner and/or focusing device configured to provide scanning of the position of the focal point of a beam in three-dimensions within a target space located near the focal point of the objective lens.

Other aspects of the invention will become apparent by consideration of the detailed description and accompanying drawings.

BRIEF DESCRIPTION OF THE DRAWINGS

FIG. 10A illustrates an image of a 4-color printed book cover using Design Type 1.

FIG. 10B illustrates a USAF 1951 Resolution Test target using Design Type 2.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Microscope Objective Lens with Integrated Wide-Field Camera

The promise of in vivo microscopy for diagnosis of diseases such as cancer is huge, and significant progress has been made to create in vivo microscopy systems. Two aspects of current state-of-the-art microscope optics are: 1) the available field of view laterally is limited to a few hundred microns, less than 1 mm, and 2) the optics are bulky, and the size of the objective lens where it is in contact with the tissue being examined is typically several mm, even in clinical microscopes designed for in vivo examination. Therefore, the tissue surrounding the small region being imaged is obscured from view.

For clinical usefulness, the microscopic cellular structure must be interpreted in the context of the larger suspicious lesion—one wants to image at the edge or the center of the lesion, and compare to surrounding healthy tissue. Therefore a solution that allows visualization of a wide field (several mm) at the surface of the tissue with precise co-registration of the microscopic field of view (less than 1 mm) is needed. The best state-of-the-art solutions allow for some mechanical guide to be attached to the tissue prior to imaging. Then a wide-field camera is attached to the guide to record an image of the tissue, after which the microscope lens is attached to the tissue, using the affixed guide to register the two fields of view. While this works for some locations on skin, it is not practical for many sites prone to development of disease, nor for tissues elsewhere in the body such as the alimentary tract.

Embodiments of the present invention address this need by providing a wide-field camera that is integrated within the bulky objective lens, providing simultaneous wide-field and microscopic views of the tissue. There is no need for a separate affixed guide, and no uncertainty due to positioning errors of the camera with respect to the microscope. The innovation deploys an ultraminiature CMOS sensor with a custom miniaturized lens that is built right into the objective lens.

Secondly, the microscope image is achieved using an annular beam in order to accommodate the obscuration due to the integrated camera. Annular beams can be shown to image living tissue as well as full circular beams, provided the central obscuration is not too large.

Figure 2:
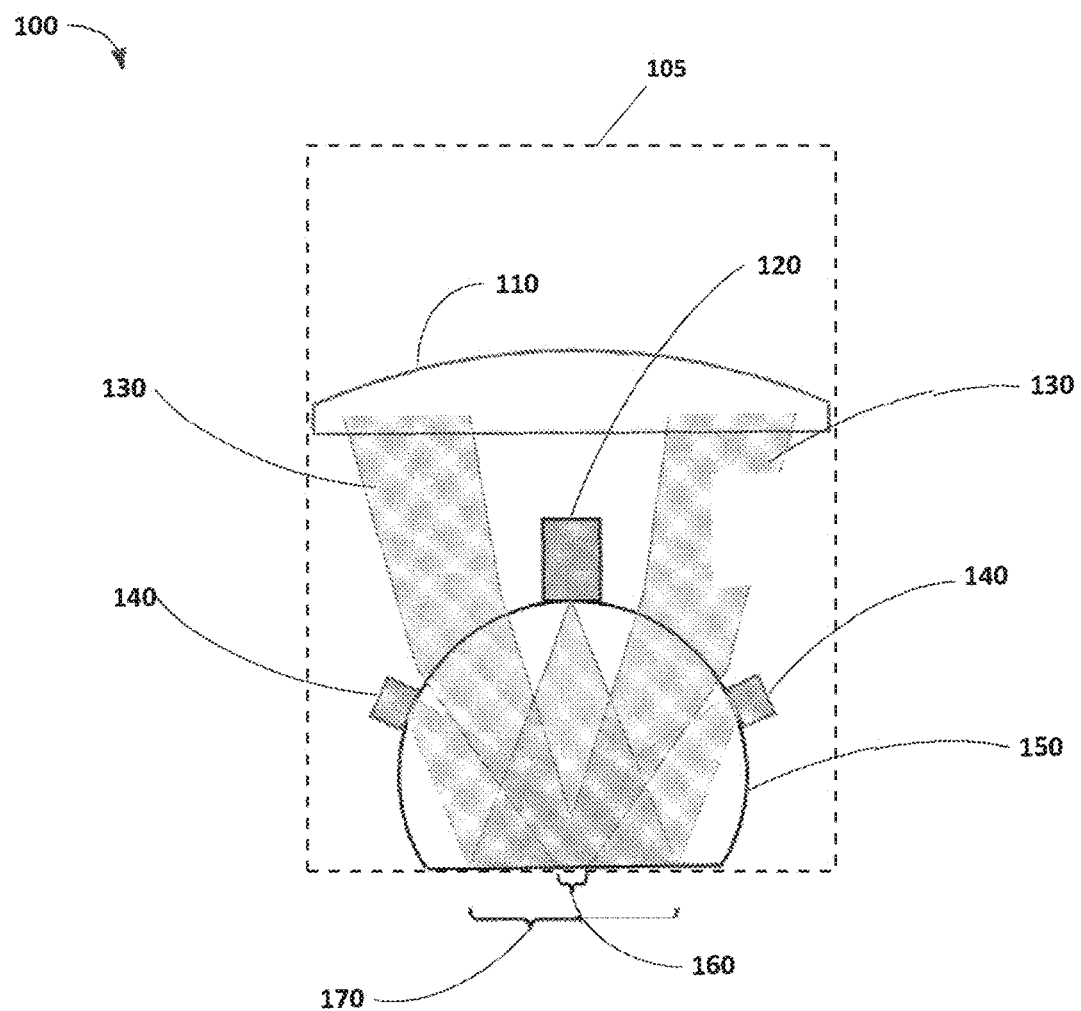
FIG. 2 schematically illustrates a high NA first lens group that utilizes a hyperhemisphere front-lens in contact with the skin, with a gap to the back lens group that is large enough to accommodate a miniature wide-field (WF) camera. The back lens is a Huvitz 0.4 NA air immersion objective lens. White light LEDs provide illumination for WF imaging.

FIG. 2 illustrates a device 100 for providing simultaneous wide-field and microscopic views of the tissue according to an embodiment of the present invention. The system 100 integrates a camera and a reflectance confocal microscope lens. The device 100 includes a housing 105, an objective lens, which comprises a first lens group 150 supported by the housing 105 and a second lens group 110 supported by the housing 105, and a camera 120 supported by the housing 105. A gap (e.g., an air gap) is present between the first lens group 150 and the second lens group 110. The gap is between 4 mm and 5 mm. More particularly, the gap is about 4.8 mm. The camera 120 is positioned between the first lens group 150 and the second lens group 110 within the gap. In one construction, the second lens group 110 is a Huvitz 0.4 NA air objective lens.

The first lens group 150 includes an hyperhemisphere lens 150 (e.g., aplanatic hyperhemisphere lens) that focuses a high-NA annular beam 130 for RCM. In other constructions, the first lens group 150 includes an hemisphere lens (e.g., aplanatic hemisphere lens). The hyperhemisphere lens 150 includes an apex. The camera 120 can be positioned at the apex of the hyperhemisphere lens 150 or to a side of the hyperhemisphere lens 120.

The camera 120 creates a central obscuration in the beam (i.e., annular pupil) for microscopy. Fortunately, the use of an annular beam for reflectance confocal microscopy does not degrade its optical sectioning property, but actually enhances it. By using an annular beam 130, the central part of the first lens group 150 is available to mount the camera 120 without affecting the confocal image. Camera 120 includes an imaging lens to view the area beneath, below, in front of, otherwise visible from the hyperhemisphere lens 150, which comprises wide-field view 170, and microscopy view 160. Microscopy using an annular pupil devotes the outer 75% of the hyperhemisphere lens to the high NA microscopic image, while reserving the central 25% for low NA, long depth-of-focus, wide-field video. The camera 120 is configured to provide video images of a target located near a focal point of the objective lens.

The device 100 also includes one or more light sources, such as light-emitting diodes 140 to illuminate the target surface. In this example embodiment, the wide-field view 170 is captured in real-time during use of the reflectance confocal microscope 100, and the microscopy view 160 is visible in the dermoscopy view. Furthermore, the camera 120 can image a surface as the instrument approaches, allowing easy placement of the probe in the context of surface features.

Figure 3:
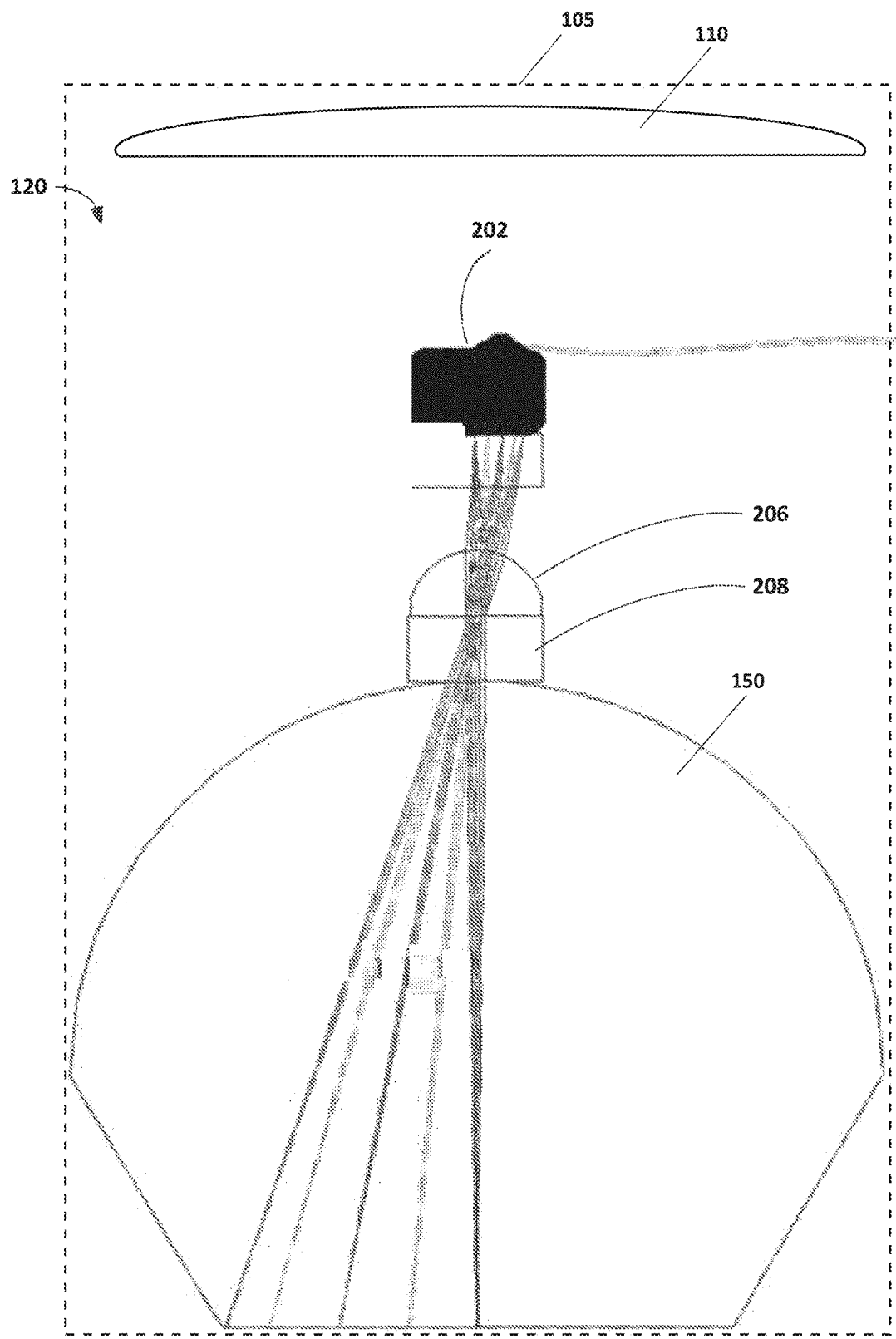
FIG. 3 schematically illustrates a camera according to an embodiment of the invention.
Figure 4:
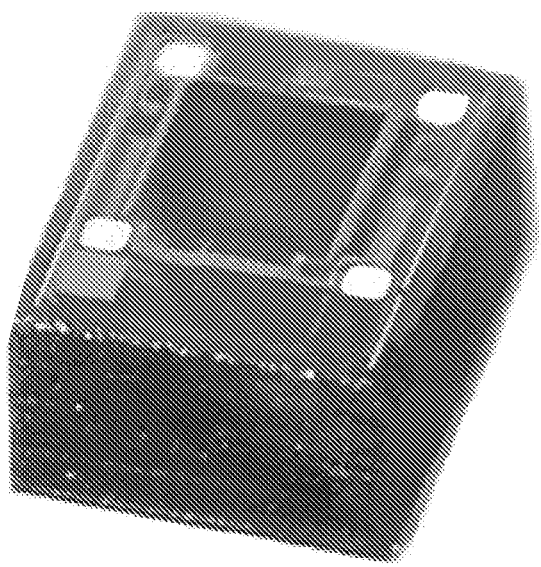
FIG. 4 illustrates an enlarged view of a CMOS sensor used in the camera of FIG. 3.

FIG. 3 illustrates the camera 120 for wide-field imaging according to an embodiment of the present invention. The camera 120 comprises a color CMOS sensor 202 (Naneye2D-RGB) from Awaiba, GmbH (now called Cmosis). See also FIG. 4. This sensor has 250×250 pixels on a 3 μm pitch, with a Bayer color mask, resulting in an active area 750 μm×750 μm. The external dimensions of the sensor are 1.03 mm×1.03 mm laterally, and 0.54 mm deep. A four wire micro ribbon cable measuring 0.72 mm×0.19 mm is soldered to the back of the sensor. The sensor includes a borosilicate coverglass (Corning Eagle XG) that is 400 μm thick.

Two singlet microlenses were designed and built. The first was a 0.97 mm focal length f/6.4 lens using a 1 mm diameter BK-7 half-ball lens, with a field of view at the sample of 2.3 mm (3.3 mm diagonal). The second was a 0.65 mm focal length f/4.3 lens using a 1 mm diameter sapphire half-ball lens 206, with a field of view at the sample of 3.8 mm (5.4 mm diagonal, limited by the 4.7 mm diameter of the hyperhemisphere surface). Details of the optical designs are provided in Table 1.

| Surface | Radius | Thickness | Glass | Diameter |
|---|---|---|---|---|
| Design 1: BK-7 half-ball lens | | | | |
| $f_{air}$ = 0.967 mm, M = −.33, FOV = 2.3 mm, F/# = 6.4 | | | | |
| Sensor | Inf | 0.400 | EAGLE | 0.750 |
| 1 | Inf | 1.000 | AIR | 1.000 |
| 9 | 0.500 | 0.500 | N-BK7 | 1.000 |
| STOP 3 | Inf | 0.500 | N-BK7 | 0.150 |
| †4 | 3.000 | 4.850 | N-BK7 | 1.000 |
| Skin | Inf | | | 3.250 |
| Design 2: Sapphire half-ball lens | | | | |
| $f_{air}$ = 0.651 mm, M = −.20, FOV = 3.9 mm, F/# = 4.3 | | | | |
| Sensor | Inf | 0.400 | EAGLE | 0.750 |
| 1 | Inf | 0.500 | AIR | 1.000 |
| 2 | 0.500 | 0.500 | Sapphire | 1.000 |
| STOP 3 | Inf | 0.500 | N-BK7 | 0.150 |
| †4 | 3.000 | 4.850 | N-BK7 | 1.000 |
| Skin | Inf | | | 4.720 |

†note there is no refraction here using index-matched glue

Figure 5:
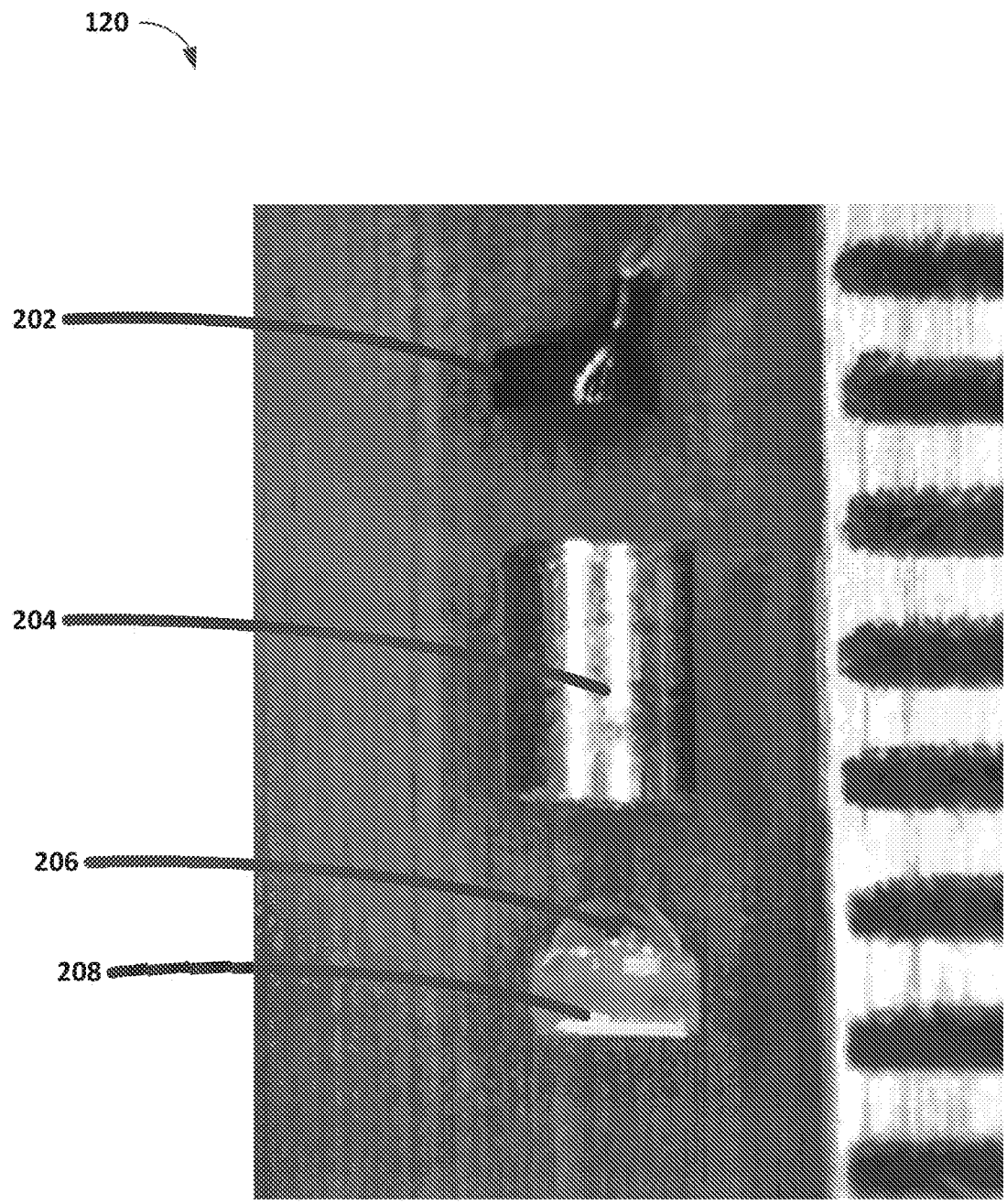
FIG. 5 illustrates an exploded view of components of the camera illustrated in FIG. 3. Scale has 1 mm rulings.
Figure 7:
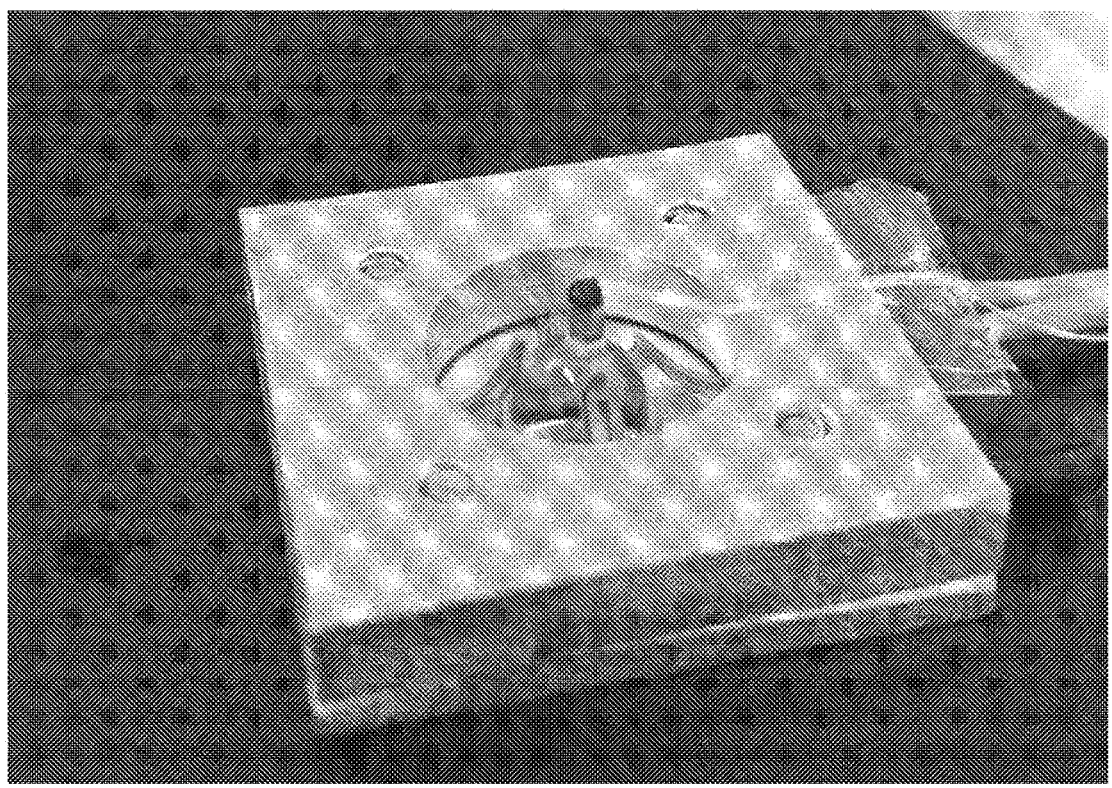
FIG. 7 illustrates the camera affixed to the apex of a 6 mm diameter hyperhemisphere lens. LEDs soldered to flexible printed circuit material provide white light illumination for wide-field imaging.

Construction of the two lenses was similar. A 500 μm thick fused silica wafer was coated with aluminum, then lithographically patterned and etched to create a fixed camera aperture. The wafer was diced into 1 mm square pieces which are referred to as "aperture blocks." Then, a half-ball lens 206 was visually aligned to the aperture and glued onto the metalized side of the aperture block 208. With reference to FIG. 5, a length of steel hypodermic tubing 204, 1 mm inside diameter, was cut and then sanded to final dimension to focus the target surface onto the sensor and control the spacing between the half-ball lens 206 and the sensor 202. The lens assembly, spacer tube 204 and sensor 202 were then all glued together. An opaque tube (not shown in FIG. 5) prevents stray light from striking the sensor. A fixture was used to actively align the microcamera to the apex of a 6 mm diameter, 4.85 mm thick hyperhemisphere lens made of BK-7 (made to specification by Optics Technology, Inc., Pittsford, NY), where it was fixed with UV cure optical epoxy. FIG. 5 shows an exploded view of a half-ball lens glued to an aperture block, a spacer element and a sensor. FIG. 7 shows the assembled microcamera glued in place on the hyperhemisphere lens 150, and held in an aluminum fixture.

Figure 6:
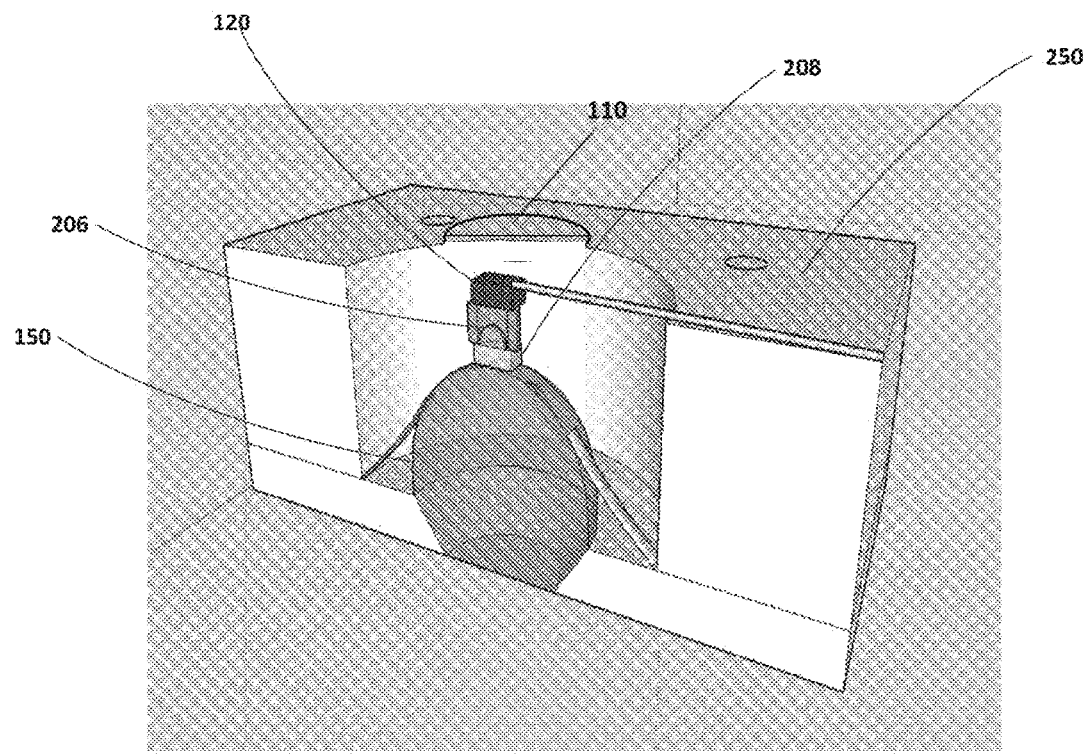
FIG. 6 illustrates a cross-section view of the camera positioned related to the objective lens.

With reference to FIG. 6, the camera 120 is illustrated attached to hyperhemisphere lens 150 according to some embodiments of the invention. In particular, the CMOS sensor 202 is attached to sapphire hemisphere lens 206 which is attached to aperture block 208 in this embodiment. Aperture block 208 is attached to the apex of hyperhemisphere lens 150 which is mounted in a support housing 250. This example embodiment illustrates one configuration integrating camera 120 into a reflectance confocal microscope.

For illumination of the target surface four white LEDs (Lighthouse A-0402UWC) were soldered to a flexible printed circuit that positions them in contact with the hyperhemisphere surface. The flexible tabs holding the LEDs are shown in FIG. 7 as well.

Figure 8:
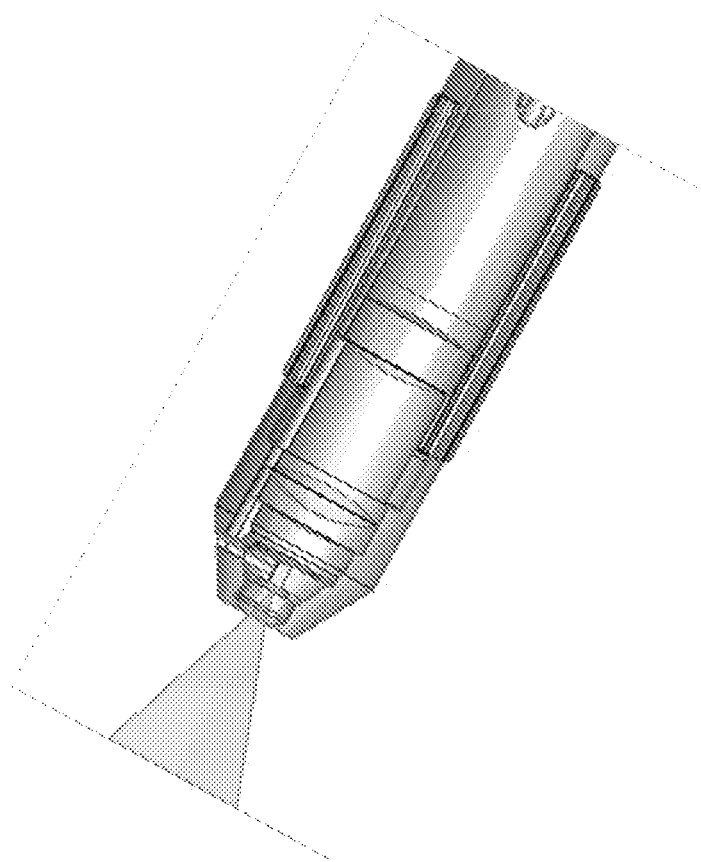
FIG. 8 illustrates a handheld probe having a larger field-of-view upon approach to a target.

FIG. 8 illustrates that the long depth of focus of the camera 120 allows endoscopic-type imaging for several mm beyond the tip of the lens, offering even wider-field images when approaching the target of interest.

Figure 9:
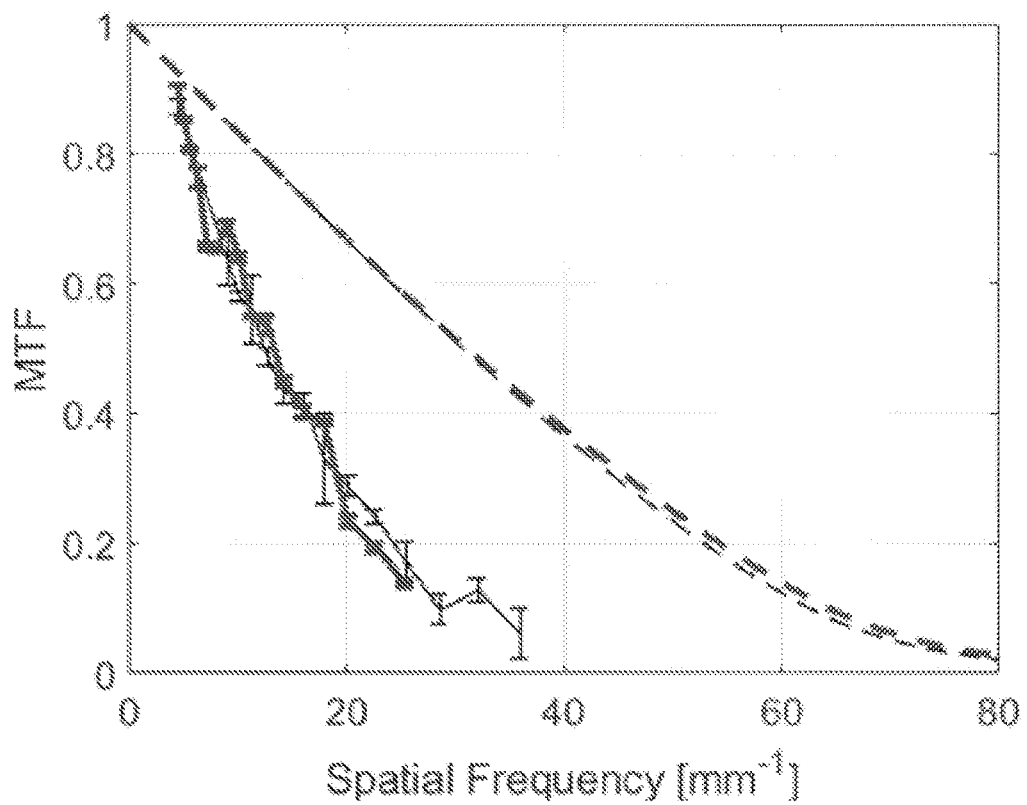
FIG. 9 graphically illustrates measured MTF for the two tested wide-field cameras (solid lines). Zemax simulated polychromatic MTF for the lenses (dashed lines). Light black lines correspond to Design Type 1. Heavy blue lines correspond to Design Type 2.

To measure the performance of the camera, a 1951 USAF bar target was imaged, which was placed in contact with the flat surface of the hyperhemisphere with water as a coupling medium. The sinusoidal modulation transfer function (MTF) values were estimated from the normalized fast Fourier transform spectra of the imaged 3 bar targets, following the method of Boreman and Yang. For these measurements, a weighted sum of the red (29.9%), green (58.7%) and blue (11.4%) channels (image luminance, based on recommendation ITU-R BT.601-7) were used. The results are plotted in FIG. 9. Measured 50% MTF frequency for both microcameras was about 13 lp/mm. Fourier analysis of this response yields an estimated 28 µm full width at half maximum (FWHM) for the corresponding line spread function. Considering only the optical performance of the lenses, the (Zemax) simulated polychromatic MTF is shown for reference, which predicts nearly diffraction limited performance for both microlens designs. The effective pixel pitch of our sensor with the Bayer color mask is 6 µm, which limits the resolution of the system. The microlenses would support higher resolution imaging if a monochrome version of the sensor was employed, or one with smaller pixels. FIGS. 10A and 10B show a representative image of a 4-color printed book cover, illustrating the color balance of the NanEye sensor with our illumination scheme.

Figure 11:
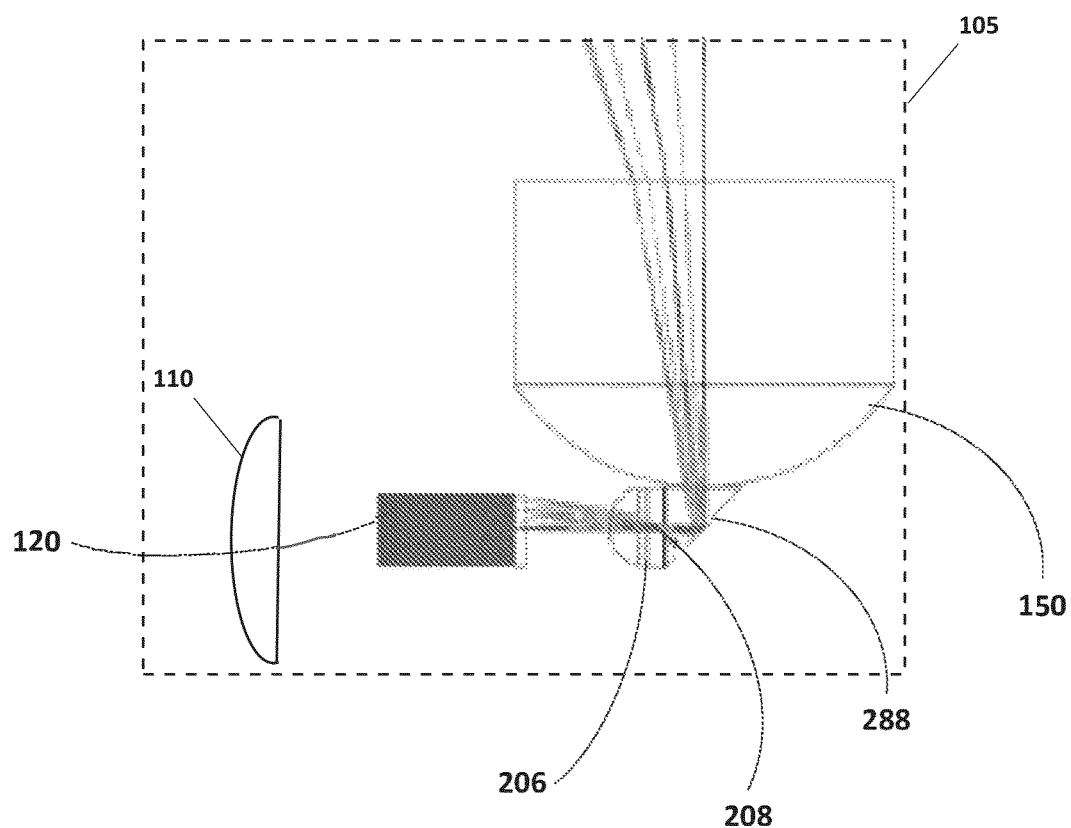
FIG. 11 schematically illustrates a camera with a right angle prism that redirects the widefield image at 90°.

Other configurations are possible, including obscuration ratios that are larger or smaller than 25%, and use of other optical configurations such as a hemisphere last lens rather than a hyperhemisphere, or some other element with or without optical power. As illustrated in FIG. 11, the camera 120 may be located at another position besides the center of the beam, and the camera lens can be separated so that only a portion of the camera lens resides on the hyperhemisphere, and a small mirror or prism 288 is used to deflect the camera light toward a CMOS or CCD or other array sensor that can be located on the side of the lens, out of the way of the microscope imaging beam. In this way a larger sensor could be used that might improve the field of view or the resolution of the image beyond what is possible with the miniature Naneye sensor.

The lens design for confocal microscopy places a nearly aplanatic hyperhemisphere in contact with skin, followed by a fully corrected back "lens group." with a 4.8 mm gap between the two. In one experiment, a long working distance 0.4 NA objective lens for this back group (Huvitz LPlan-Fluor 20λ, WD=12.2 mm) was used. The effective NA of the compound lens is 0.9. A central obscuration due to the wide-field camera results in an annular pupil with an obscuration fraction (ε) of 0.17. Scanning is telecentric, with the galvanometer scanners being imaged to the back aperture of the Huvitz lens. The thickness of the 6 mm diameter hyperhemisphere was 4.85 mm, chosen to minimize spherical aberration when focusing to a depth of 70 µm inside the tissue. The depth at which the beam is focused is controlled by adjusting the spacing between the hyperhemisphere and the Huvitz lens. Confocal imaging was performed with a laser wavelength (λ) of 648 nm.

Figure 12:
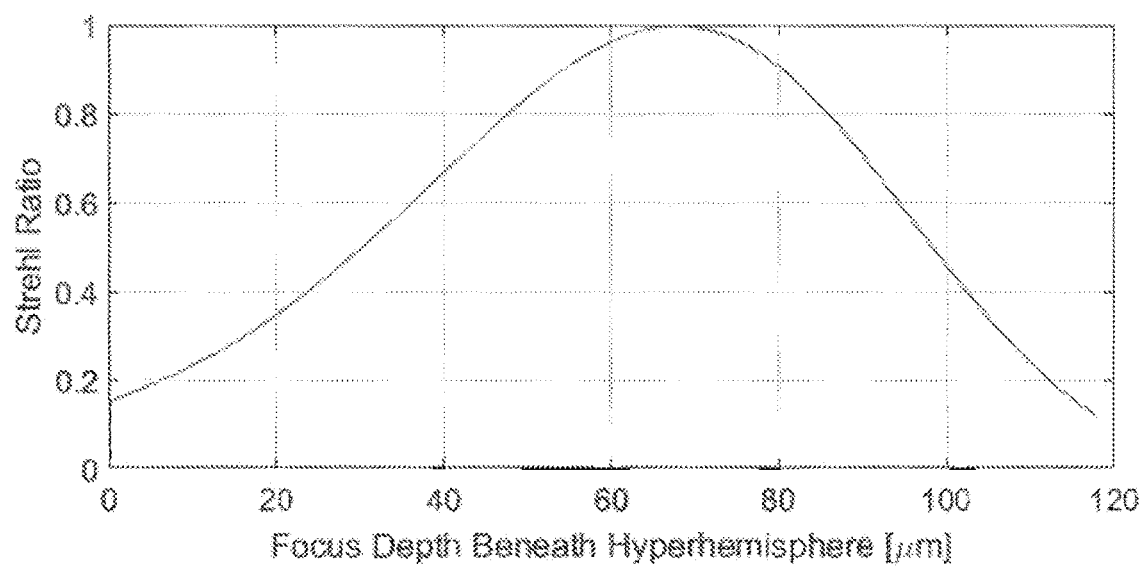
FIG. 12 graphically illustrates simulated Strehl ratio for the microscope objective lens, as a function of depth at which the beam is focused into the tissue.

Simulated performance of the lens is summarized in FIG. 12, which plots computed Strehl ratio of the focused beam on axis as a function of imaging depth. The dominant aberration is uncorrected spherical. There is an axial range of about 40 µm, centered at 68 µm, with Strehl>0.8. Typically, this includes the depth at which one finds the diagnostically important basal cell layer and dermal-epidermal junction in skin, which was our design intent. The simulated Strehl ratio exceeds 0.2 for depths from 6 µm to 112 µm. Increasing spherical aberration, combined with tissue scattering loss, will limit the maximum imaging depth for this lens design.

Image quality for reflectance confocal microscopy in scattering tissue is improved by using a finite-sized pinhole, which helps to reduce coherent speckle. In the instrument, a pinhole aperture with a radius $r_p$ was used that is 2.4 times the Airy radius, measured to the first zero for the diffraction limited beam. It has been shown that, with a finite sized pinhole, optical sectioning is also improved with an annular aperture, so that the inclusion of the wide-field camera in the lens does not degrade the optical sectioning, but, in fact, enhances it. With obscuration ratio ε=0.17 for the system, the optical sectioning in terms of the FWHM of the axial point spread function (PSF) is theoretically reduced, though the improvement is modest, and less than 10%.

Figure 13:
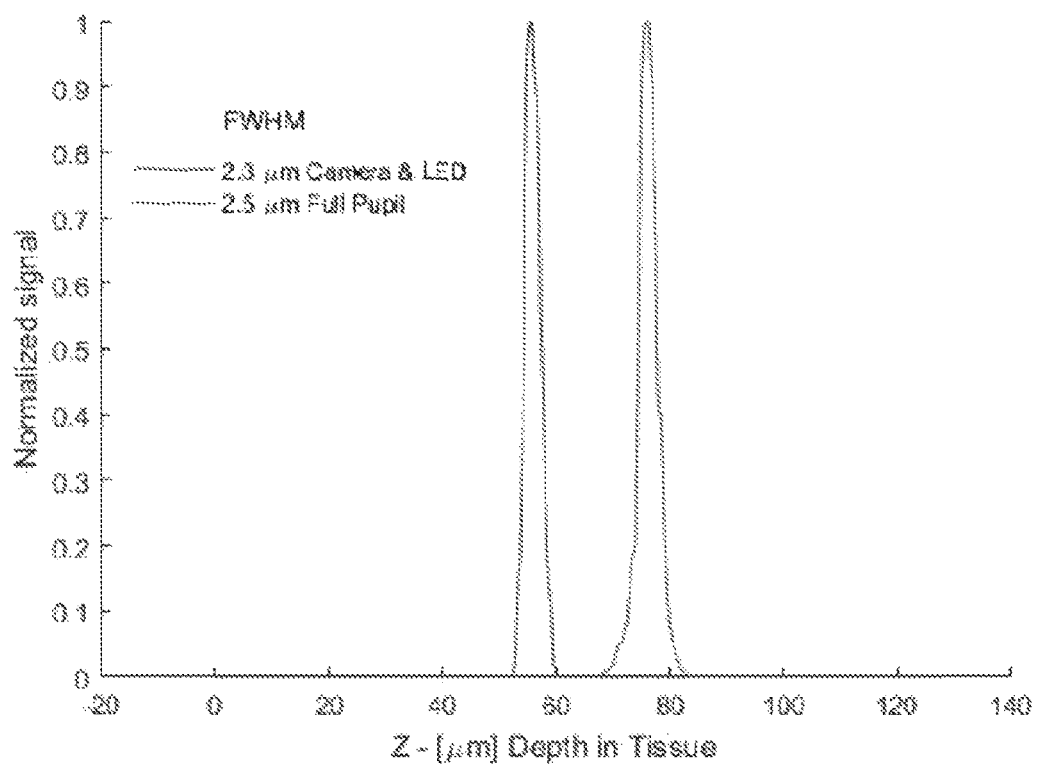
FIG. 13 graphically illustrates axial PSF of full pupil system, compared to camera-LED setup.

FIG. 13 shows the axial PSF measured by translating a plane mirror through the focal region of our compound lens, with the wide-field camera and LED illumination "tabs" in place. The coupling medium between the hyperhemisphere and the mirror was water with refractive index of 1.33, close to the anticipated index of refraction for skin. A minimum FWHM of 2.3 µm (average of 3 measurements) was measured with the system focused at a depth of 50 um below the hyperhemisphere surface. With the system focused shallower or deeper, the FWHM degrades fairly quickly. For comparison, the measurements were repeated using a hyperhemisphere with a clear aperture without wide-field camera or illumination LEDs. The minimum FWHM was found to be 2.5 µm (average of 3 measurements) confirming that the annular aperture improves the measured optical sectioning when using a finite sized detection pinhole 2.4 times bigger than the Airy spot.

Figure 14A:
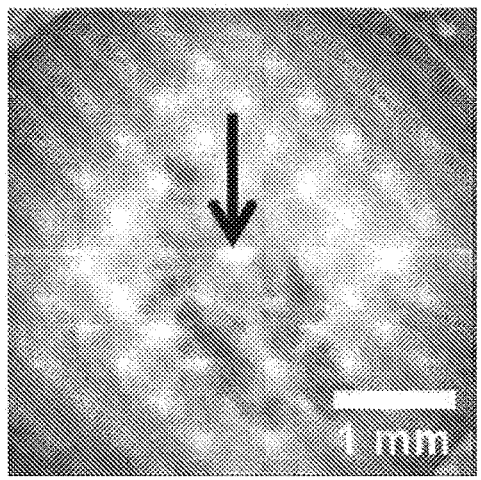
FIG. 14A is a wide-field image of pigmented lesion from a volunteer.
Figure 14B:
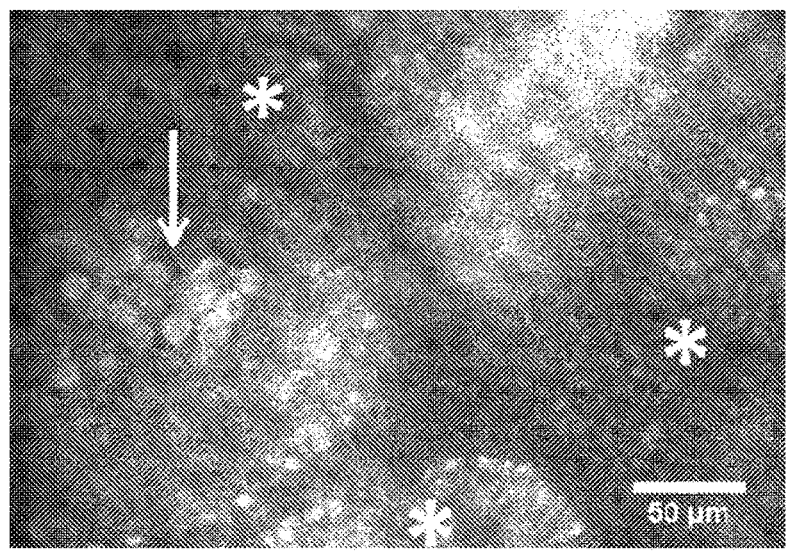
FIG. 14B is a corresponding RCM image from the center of the wide-field image in FIG. 14A.

Using a benchtop scanning reflectance confocal microscope that has been described previously, the integrated wide-field camera was used to guide subsurface RCM imaging of pigmented lesions in vivo on 30 volunteers, recruited under an IRB-approved protocol. A representative image pair in FIGS. 14A-B show a wide-field color image (FIG. 14A) of a pigmented nevus (mole) on the forearm of a volunteer, with the corresponding grayscale RCM image (FIG. 14B). The raster scan of the confocal microscope is seen at the site within the nevus (black arrow) where a video and stack of RCM images were acquired. The wide-field image shows a globular pattern of brownish-black pigmentation. The RCM image shows clusters of small bright basal cells (*) at the dermal-epidermal junction, and a single cluster of larger and brighter roundish-appearing nevocyte cells in the dermis (white arrow). Scale bar is 1 mm (wide-field image) and 50 µm (RCM image). The accompanying video (Visualization 1) shows superficial granular and spinous layers, consisting of a pattern of dark nuclei within bright grainy-appearing cells, and, as is also seen in FIG. 14B, the underlying deeper clusters of basal cells and nevocyte cells. The clearly resolved features in the different cell layers, particularly, nuclei in the basal layer, confirms the excellent optical sectioning performance of the compound lens.

In-Lens Scanner

It is customary for laser scanning imaging systems (two examples are confocal microscopes and two photon microscopes) and exposure or marking systems (for example a two-photon 3D lithography system) to use a beam scanner that is separate from the well-corrected imaging lens. Often an optical relay forms an image of the scanner in the back focal plane of the imaging lens for telecentric scanning. In other cases non-telecentric scanning is satisfactory for the application, and no relay optics may be present, or a relay that does not result in telecentric scanning is used. The essential observation is that the scanner and the lens are separate entities, independently optimized.

Embodiments of the invention include the scanner as part of the lens, merging the functionality of beam focusing and scanning into a single functional unit. The essential feature is that the optical prescription of the scanner is included in the design and optimization of the lens, where the prescription of the scanner is variable depending on the position of the scan.

In the simplest situation, the optical prescription of the scanner is to impart an optical wavefront phase that varies linearly in one spatial dimension. This is the case for a tilting mirror, for example, or a transparent spatial light modulator imparting a phase delay that varies linearly with one spatial dimension. An optical beam receiving this linear phase modulation will be deviated in its direction of propagation.

If the scanner can modulate the optical phase with some more complex dependence on the spatial variables, then wavefront curvature or aberrations may be controlled. The curvature and aberrations may be varied in concert with the linear phase components.

Under this invention, the design of the imaging or marking lens includes the influence of the scanner on the optical wavefront in order to achieve the desired performance that includes both focusing and scanning the beam. To reiterate, the influence of the scanner may be only linear dependence on spatial variables (tip/tilt), or may include quadratic dependence (focusing) or may include also higher order dependence (aberrations of various types and orders).

An advantage of including the scanner properties in the lens design is a simplification of the lens. For example, a so-called Plan type objective lens devotes glass surfaces to removing field curvature. If a scanner can adjust its quadratic phase in concert with its linear phase to compensate for field curvature, then flat-field operation is possible with a simpler and less expensive lens. Similarly, with higher order aberration compensation other glass types and surfaces may be eliminated from the lens design to improve overall cost and performance.

An additional advantage of including the scanner in the lens design is to minimize the overall footprint of the scanned laser imaging system or marking system or lithography system. Placing the scanner in the lens or near the lens may obviate the need for relay optics and may provide the essential functionality of scanning and focusing the beam in a very compact optical element.

In one implementation a tip/tilt platform with a deformable mirror surface as the beam scanner. The mirror is integrated into a first lens group, e.g., an objective lens, with lens elements both preceding and following the scanner. The system further incorporates a folded, annular beam in order to incorporate both transparent lenses and the reflective tip/tilt/deformable mirror. Optimization of the system includes the prescription of the glass surfaces, which are fixed, and the prescription of the deformable mirror, which can be changed in concert with the amount of tip or tilt, in order to minimize aberrations throughout the field of view of the instrument. This invention could equally apply to a transparent scanner, such as a spatial light modulator, instead of the reflective tip/tilt/deformable mirror.

The specific application for this example of the invention is a handheld scanning laser microscope for imaging of skin or intraoral tissue for disease diagnosis, with cancer a prominent example. Confocal reflectance microscopy, confocal fluorescence microscopy, two-photon excitation fluorescent microscopy and second harmonic generation microscopy are all scanning laser microscope imaging modalities that may be useful in this context, and may benefit from this invention.

Among several optical technologies that are being translated for noninvasive detection of cancer, reflectance confocal microscopy has shown significant success for screening and diagnosis of skin malignancies in vivo while reducing unnecessary biopsy of benign lesions, guiding surgery by detection of cancer margins without the need for biopsies, and by monitoring patients post-treatment without requiring further biopsies. Initial success is being seen, too, for the detection of oral lesions. Despite all of this promising progress, the large size of the microscope remains a huge barrier against wider acceptance and routine clinical use, in response to which significant effort has been made to engineer smaller in vivo confocal microscopes. But endoscopic reflectance confocal microscopy does not yet enjoy widespread clinical use. To meet the challenges of diagnostic imaging in a clinical setting, miniaturization is not enough. The imaging system must still deliver high-resolution images with excellent contrast. The large NA necessary for good optical sectioning and high signal-to-noise ratio demands that spherical aberration be managed. The desired image "plane" is seldom en-face, but could be any oblique or vertical section of the tissue depending on the lesion to be imaged, requiring an agile 3D beam scanning capability. Furthermore, the clinician needs to know just where the microscopic image is being formed in the context of the gross morphology of the tissue, yet the field of view one can see through a typical microscope objective is only a few hundred microns; the large lens obscures the rest of the tissue from view. By contrast, the miniaturized probes developed to date have exhibited compromised image quality, and without wide-field image guidance, the usefulness of these miniature probes for disease diagnosis is severely diminished.

Not only for endoscopy, but also for dermatology the size of the instrument remains a limitation. Skin cancers, especially, lentigo maligna melanomas and non-melanomas (basal- and squamous cell carcinomas), occur mostly (about 80%) on the face and head-and-neck areas, in "nooks and crannies" around the nose, ears and eyes. Other types of melanoma occur under the nails, between fingers and toes, for which the currently available microscope remains quite inadequate. For intraoperative mapping of basal cell carcinoma margins, to guide Mohs surgical excision, imaging must be performed within small and deep crater-shaped wounds of typical extent 5-10 mm, for which, again, currently available microscopes are too large. Thus, for dermatology, too, there is a need for smaller "pencil" sized reflectance confocal microscopes, but only if the solution maintains image quality, flexibility, and wide-field image guidance. It is precisely this challenge that is being addressed in developing the iLSM technology and handheld probes based on this approach.

A small-size confocal microscope will be clinically useful provided it delivers 1) diagnostic quality images at all depths and at appropriate orientations, permitting enhanced examination of deeper tissue, 2) a wide-field camera image to guide the location for microscopic tissue examination, and 3) ease, speed and efficiency of use for "seamless integration" into today's fast paced workflow of clinical practice. Miniaturized laser scanning microscopes have been previously developed, but have had limited clinical impact because they suffered from compromised optical performance that does not clearly show nuclear-level detail, they lacked agile 3D beam scanning to allow arbitrary oblique sectioning, and, importantly, they had no means for co-registered wide-field imaging to provide context for the very small field of view imaged by the microscope. A small laser scanning microscope that overcome these deficiencies would significantly expand the coverage of confocal microscopy for skin, and translate its diagnostic potential to epithelial cancers occurring elsewhere in the body.

A new class of "active objective lens" has been developed that co-locates wide-field endoscopic or dermoscopic imaging with high-resolution (i.e., with high numerical aperture (NA)) 3D tissue microscopy in a single sub-cm sized instrument called the integrated laser scanning microscope (iLSM). The technology is adaptable to many modalities including reflected light confocal and fluorescence confocal, two-photon fluorescence or optical coherence microscopy. This invention provides a new technology platform for development of in vivo microscopes for skin, oral, cervical, GI and other cancers.

The most significant limitations of miniaturized laser scanning microscopes: 1) agile 30 beam scanning for image acquisition along en face, oblique or vertical cross sectional planes, employing an active optical system, and 2) the integration of continuously co-registered wide-field video to locate the microscopy image with respect to surface tissue morphology are addressed. This integrated laser scanning microscope, or iLSM, represents a novel approach to solve the challenge of achieving simultaneous 3D microscopy and wide-field video imaging in an optical system of optimized size, small enough for incorporation into a handheld pencil probe or endoscope, but large enough to maintain high NA and excellent confocal image quality.

One goal to shrinking the iLSM for skin and intraoral imaging is a novel beam scanning element capable of scanning a high NA beam throughout a three dimensional space. Because full 3D scanning is achieved by reflection from a single active surface, the scanner is designed into the objective lens, with no relay optics or other extra elements. The first specific aim is development of this scanner which comprises a variably curved mirror for focus control (z scan) on a tip-tilt platform, (lateral x-y scan), with electronic control over beam position in all three axes. Key performance includes lateral scanning at up to 8 frames per second, fast focus scanning over a range of 150 µm in tissue at up to 10 kHz enabling en face, oblique or vertical cross sectional imaging, and dynamic control of spherical aberration at all depths. The MEMS scanner will be fully characterized with respect to optical and mechanical performance, relative to the clearly defined specifications required for the iLSM instrument. In other embodiments, the beam scanner may comprise a liquid crystal spatial light modulator.

The target specifications for a first generation iLSM are given in Table 2, for both microscopic imaging and wide-field video imaging. It is noteworthy that the 3D diffraction-limited field of view (Strehl>0.8) for this proposed instrument using active optics exceeds what is possible with a highly corrected static objective lens, which necessarily suffers from spherical aberration when imaging at different depths through stratified tissue. The color video image will function as an endoscopic camera; scaled appropriately for handheld use, the field of view of this image will be comparable to that of a conventional dermoscope.

TABLE 2 iLSM Optical Performance Specifications

| 3D Laser Scanning Microscopy Performance | Wide-field Video Performance |
|---|---|
| N/A = 0.75 | F# 6 aperture |
| FOVxy > 300 µm | full color imaging |
| FOVz, >150 µm (full focus range) | 250 × 250 pixels |
| Active correction of spherical aberration | FOV 2-7 mm at tissue surface, depending on instrument scaling |
| Supports active x-y-z scan trajectories including en face, oblique or vertical planes Frame rates up to 8 frames-per-second | FOV 60° in air (endoscopic/proximity imaging) 44 frames-per-second |

Figure 1:
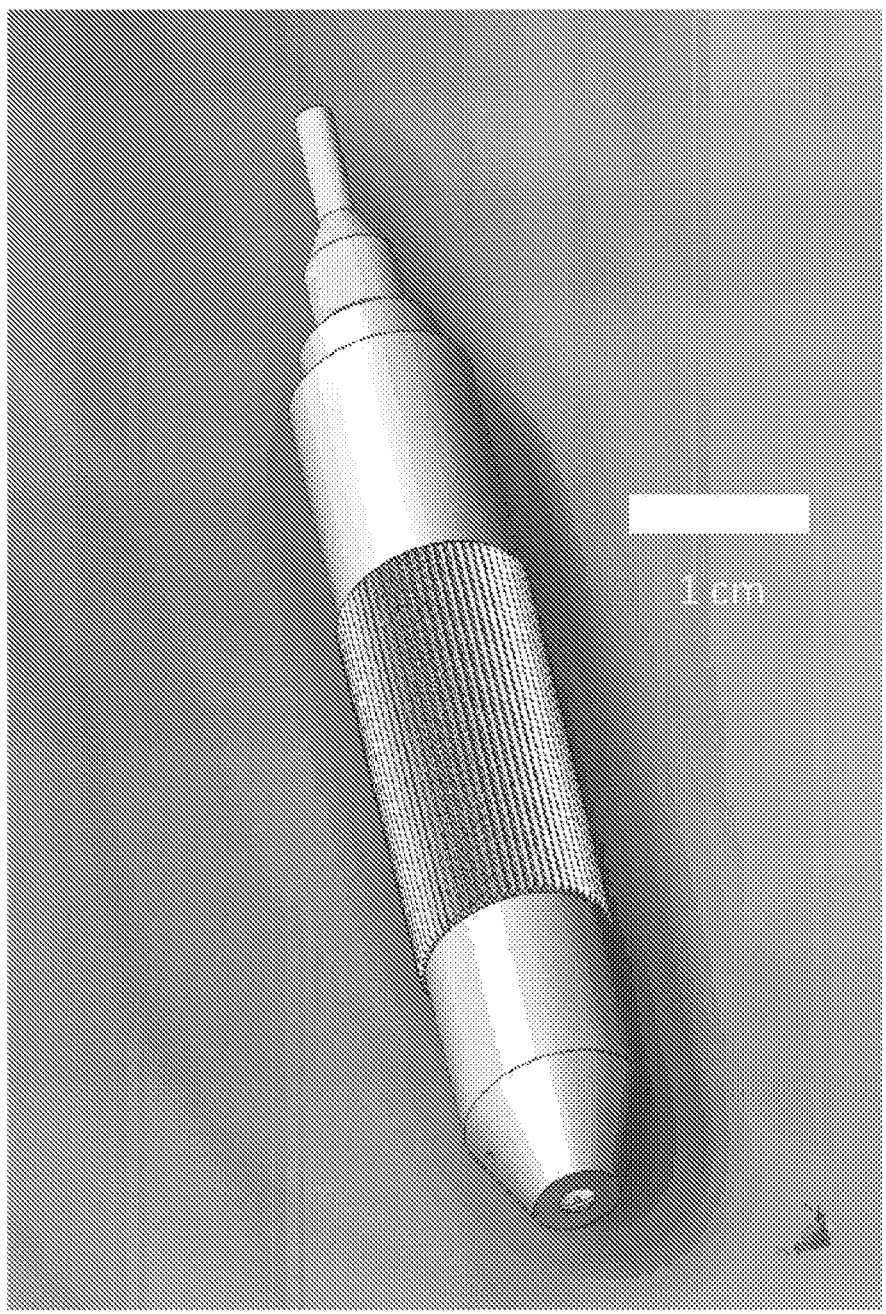
FIG. 1 illustrates a handheld dual-view microscope providing wide-field dermoscopy with simultaneous reflectance confocal microscopy according to an embodiment of the invention.

FIG. 1 illustrates the size of the iLSM module. The iLSM is functionally an infinity-corrected objective lens with a built-in beam scanner and wide-field CMOS camera. A complete instrument minimally adds to the iLSM an illumination/detection fiber and collimating lens, but could also include other optics which would be housed in the handle of a pencil probe or right-angle intra-oral probe.

MEMS 2D beam scanning is an enabling technology for distal-scanning endoscopic and handheld confocal microscopes and OCT imaging systems. Millimeter dimension MEMS gimbal tip-tilt mirrors have achieved high resolution of more than 500 resolvable spots and real-time scanning up to 60 frames-per-second. Control of the third (z) dimension has been more challenging. The first MEMS-based confocal microscope with a deformable mirror for focus control was mentioned in 2000. The same mirror simultaneously could correct spherical aberration. In 2004, Shao demonstrated the first integrated 3D MEMS beam scanner that placed a deformable mirror on a tip-tilt gimbal and proposed a confocal microscope architecture with annular pupil that fit within a 2 mm diameter probe tip.

This 3D MEMS mirror technology forms the basis of the active-optics iLSM, delivering agile x-y-z scanning with built-in correction for depth-dependent spherical aberration. Shao's 3D MEMS mirror had limited range of focus, about ⅕ what is required for the iLSM. Since that time, new membrane materials and deformable mirror architectures have been discovered to achieve a five-fold improvement in focus control range.

Figure 15:
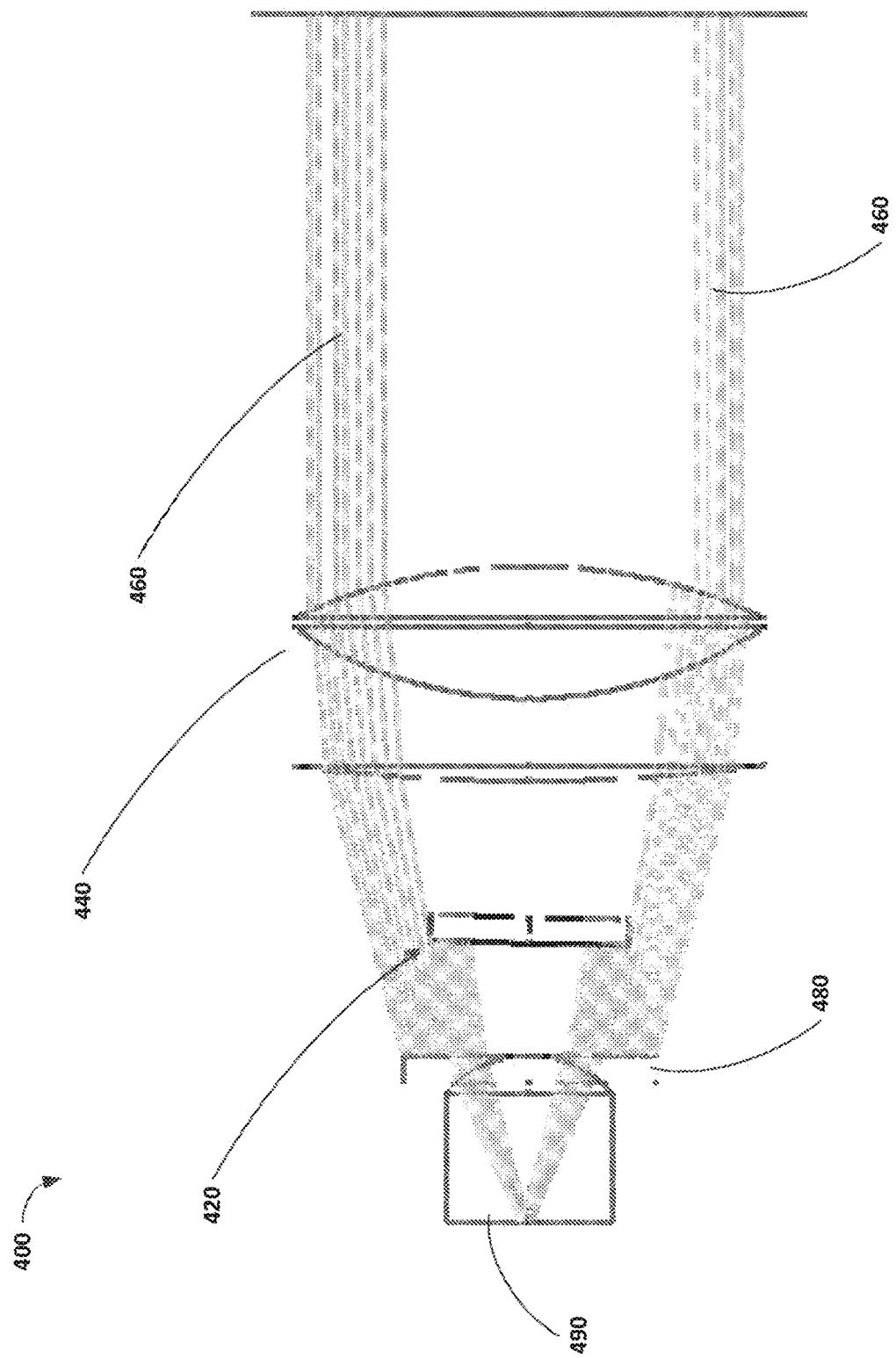
FIG. 15 illustrates a MEMS scanner integrated into an objective lens of a microscope according to an embodiment of the invention.

With its ability to change the wavefront curvature and correct dominant spherical aberration, the new MEMS tip-tilt-focus mirror enables another innovation, which is to place the scanner within the objective lens, rather than using a bulky external lens relay to image the scan mirror to the back focal plane of the objective lens. FIG. 15 illustrates the MEMS scanner 420 as being the second optical element, counting from the tissue surface, the tissue being in contact with a high index-of-refraction hyperhemisphere front lens. All of the glass optics after the MEMS scanner 420 must only be designed for a fixed, on-axis conjugate, greatly simplifying the optical design. A second flat annular reflector and doublet 440 serve to perfectly collimate the beam, completing the iLSM module. The pupil is an annulus, and the instrument maintains axial symmetry of the optical path.

A ray trace simulation of the iLSM using Zemax optical design software validates the performance of this proposed architecture, which is capable of Strehl>0.8 over the full 3D microscopic imaging volume of 300 µm laterally and 150 µm axially. The optical requirements set the mechanical requirements of the MEMS mirror, which are summarized in Table 3. Those performance specifications are within the range of what has previously been achieved for both gimbal mirrors and deformable focusing mirrors, and the iLSM x-y-z scan mirror will achieve the necessary performance metrics for the iLSM.

FIG. 15 illustrates an embodiment of a system 400 including a MEMS scanner within an objective lens. Reflective variable focus lens 420 changes its spherical curvature and corrects dominant spherical aberration allowing the MEMS scanner to be located within the objective lens in this example embodiment, rather than using a bulky external lens relay to image the scan mirror to the back focal plane of the objective lens. In this embodiment, beams 460 reflect from annular reflector 480 to reflective variable focus lens 420. Annular reflector and a doublet 440 serve to collimate the beam. In order to both scan and focus across the x, y, and z axis, reflective variable focus lens 420 changes curvature and corrects dominant spherical aberration with control over the surface shape (for z scanning), while reflective variable focus lens 420 is mounted as a gimbal to achieve lateral x-y scanning (further specified in FIGS. 18 and 19), in this example embodiment. Reflective variable focus lens 420 has functions over the full lateral and axial extent of the microscopic fields of view of hyperhemisphere front lens 490.

Confocal microscopy using an annular pupil has been well studied. It is commonly known that a thin annulus with a point detector produces better lateral resolution, but exhibits diminished axial sectioning, compared to a circular pupil. Yet with a finite sized pinhole (desirable and usual for suppressing speckle for in vivo images), an annular pupil with 50% obscuration as we have adopted in our proposed design, actually offers better axial sectioning with lower axial sidelobes. The speckle suppression using a finite-sized pinhole combined with recovered resolution with an annular pupil was nicely demonstrated using a scattering phantom, while the annular pupil can also improve signal/background ratio in the presence of diffuse scatter. But reflected light confocal microscopy of human skin has not previously been demonstrated using an annular pupil.

Figure 16:
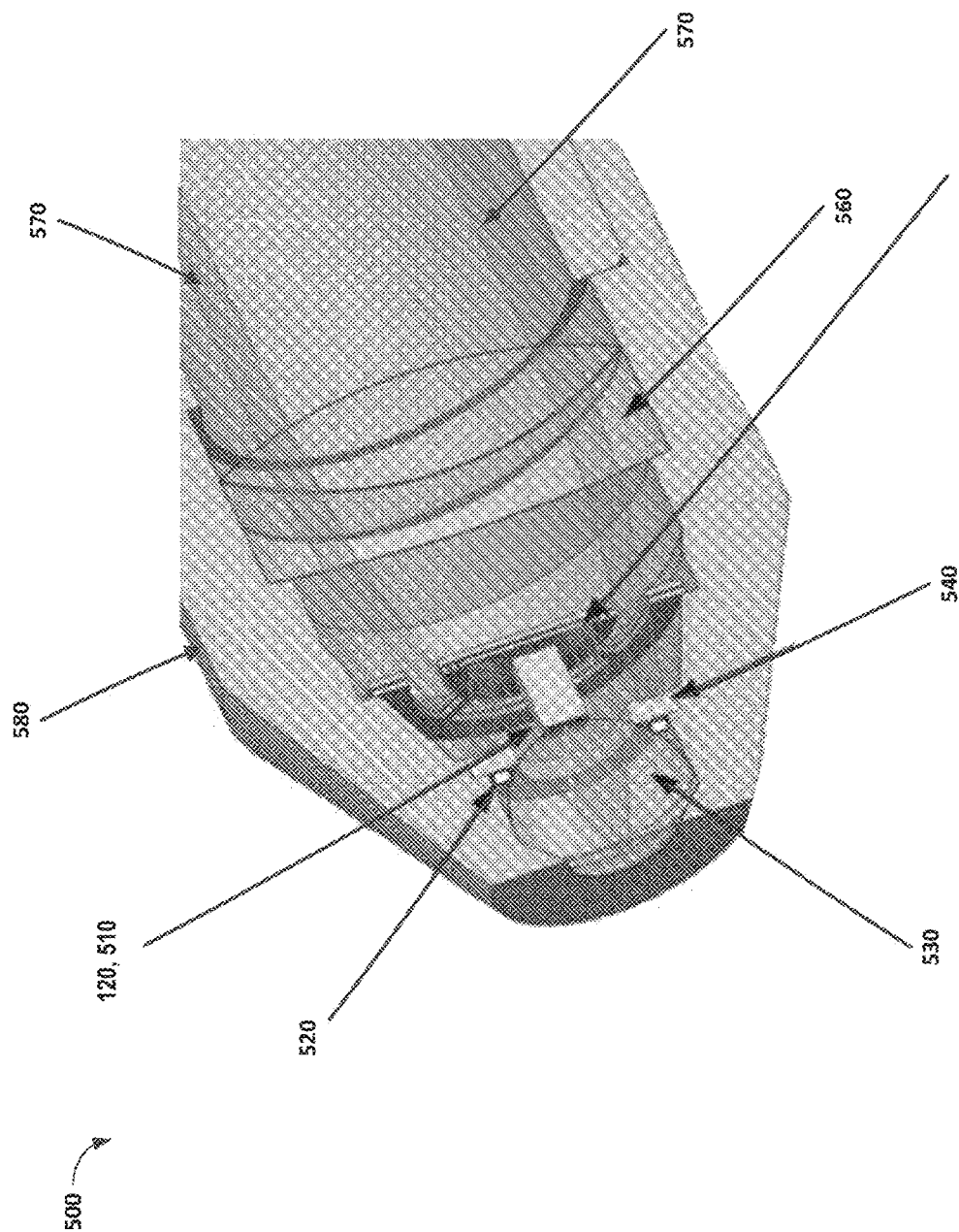
FIG. 16 illustrates an assembly of a camera and a MEMS scanner integrated into an objective lens of a microscope.
Figure 17:
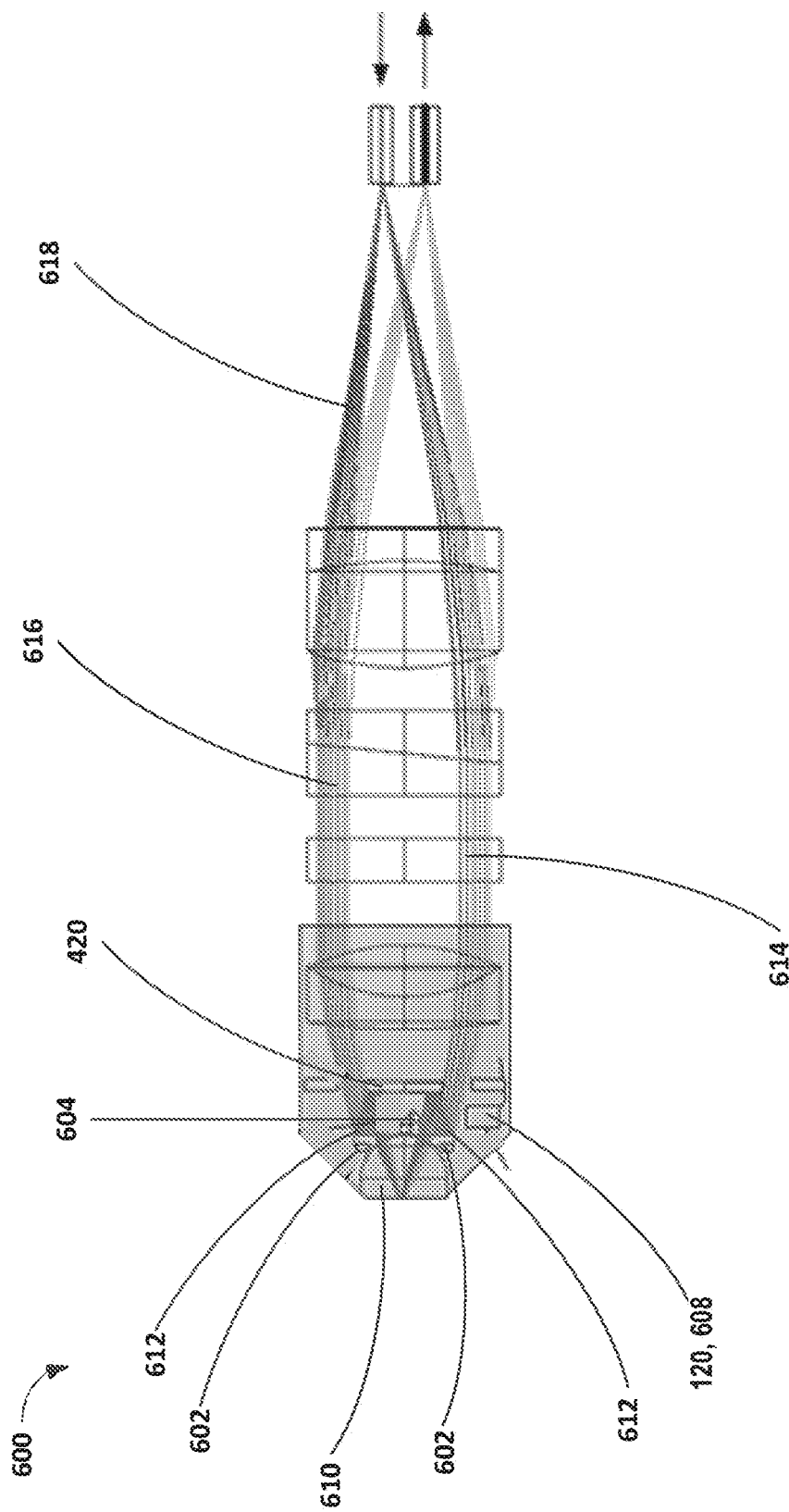
FIG. 17 illustrates a cross-sectional view of a reflectance confocal microscope with a MEMS scanner and a camera integrated into an objective lens of the microscope. A single mode polarization maintaining fiber provides laser illumination while a larger core fiber is used for detection to increase signal and reduce speckle.

The second innovation is the integration of wide-field video imaging into the iLSM for guided confocal imaging. To date no system has been developed that can simultaneously achieve high NA microscopy and wide-field video of overlapping regions. A new millimeter-scale CMOS video camera (described above) will be used to place the video path directly in the objective lens. The annular pupil devotes the outer 75% (by area) of the hyperhemisphere lens to the high NA microscopic image, while reserving the central 25% doublet for low NA, long depth-of-focus, wide-field video. FIG. 16 illustrates the concept (not quite to scale). The NanEye CMOS camera from Awaiba uses a 0.7×0.7 mm2 active area, and has dimensions of only a 1×1×2 mm (details above). The image field is 60° in air (32° in the glass). Depending on scaling of the probe, the field of view at the tissue when in contact with the glass surface may be between 2 and 7 mm. The long depth of focus of the camera allows endoscopic-type imaging for several mm beyond the tip of the iLSM, offering even wider-field images when approaching the tissue surface (FIG. 8). The camera itself may be located directly behind the first lens element (as in FIG. 16), or may be located at the edge of the assembly, using a right-angle reflecting prism (FIGS. 11 and 17). In this way the MEMS scanner and video camera may both be accommodated at their optimal separations, without causing the iLSM size to increase. The camera requires white light illumination at the probe tip. This will be accomplished with chip LEDS mounted on the back side of the annular mirror shown in FIGS. 16 and 17.

Zemax ray tracings have been performed to validate the video imaging performance and confirm that a microlens as fast as F #6 can be used while maintaining nearly diffraction limited MTF over the full image field of the camera.

A representative instrument using the iLSM is the two-fiber confocal microscope illustrated in FIG. 17. Here polarization maintaining single-mode fiber delivers laser light to the microscope. A Wollaston prism directs the beam toward the iLSM, passing through a quarter-wave plate to create circularly polarized light. The backreflected light from the tissue is converted to the orthogonal polarization state, separated at the prism and coupled into a large core detection fiber with finite-sized pinhole filter, with pinhole size chosen large enough to minimize speckle in the image but small enough to ensure adequate axial cross sectioning. The wide-field camera is located to one side, with a right-angle reflector at the apex of the hyperhemisphere (also the location of the aperture stop for wide-field imaging). An appropriate dichroic filter over the camera will prevent scattered laser light from corrupting the white-light image. This design is intended to be illustrative of the future utility of the iLSM. Other microscopic imaging modalities can be equally well supported including fluorescence confocal, two-photon excitation fluorescence and optical coherence microscopy.

The early 3D MEMS scan mirrors developed by our group deployed a deformable membrane of metalized silicon nitride on a tip-tilt gimbal. Two annular electrodes allowed independent electrostatic control of beam focus and 3rd order spherical aberration. This scanner led to an ultra-miniature fluorescence confocal microscope with NA=0.4. The deflection stroke of that MEMS scanner was limited to about 3 μm—the iLSM will demand a 5× increase in focus control, owing to its higher NA and deeper depth of penetration. Our group has worked for the last decade to improve the stroke and speed of electrostatic deformable mirrors, and have recently achieved mirrors with more than 16 μm stroke that are capable of full depth focus scanning at speeds exceeding 10 kHz. These new mirrors use metalized polymer membranes (the photoset polymer SU-8), and their dynamic performance is optimized with carefully engineered viscous air damping. Three annular actuation electrodes allow shaping the deformed membrane to control spherical aberration out to the 5th order simultaneously while positioning the focus of the reflected beam.

Figure 18:
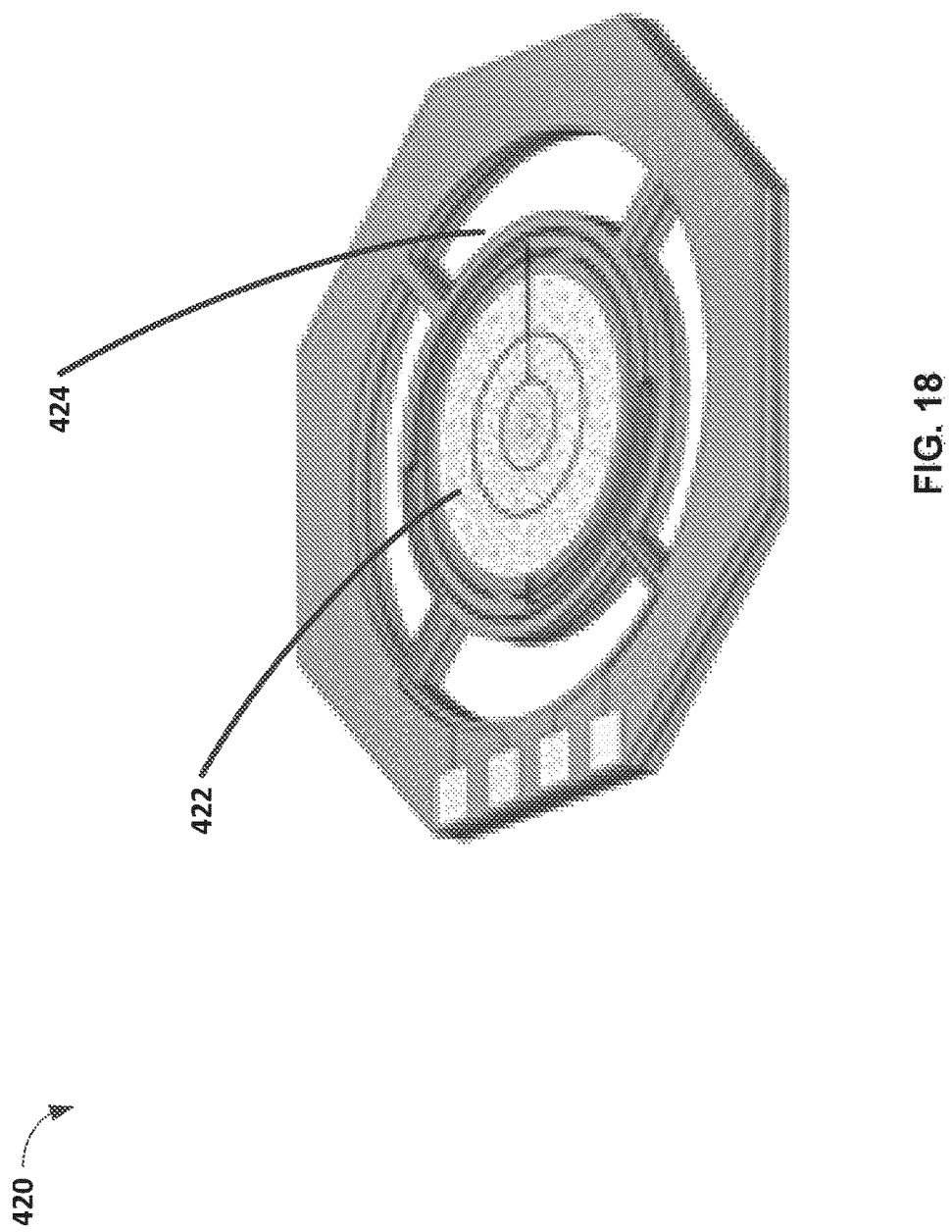
FIG. 18 illustrates a scanner with deformable polymer membrane supported on a silicon gimbal according to an embodiment of the invention.
Figure 19:
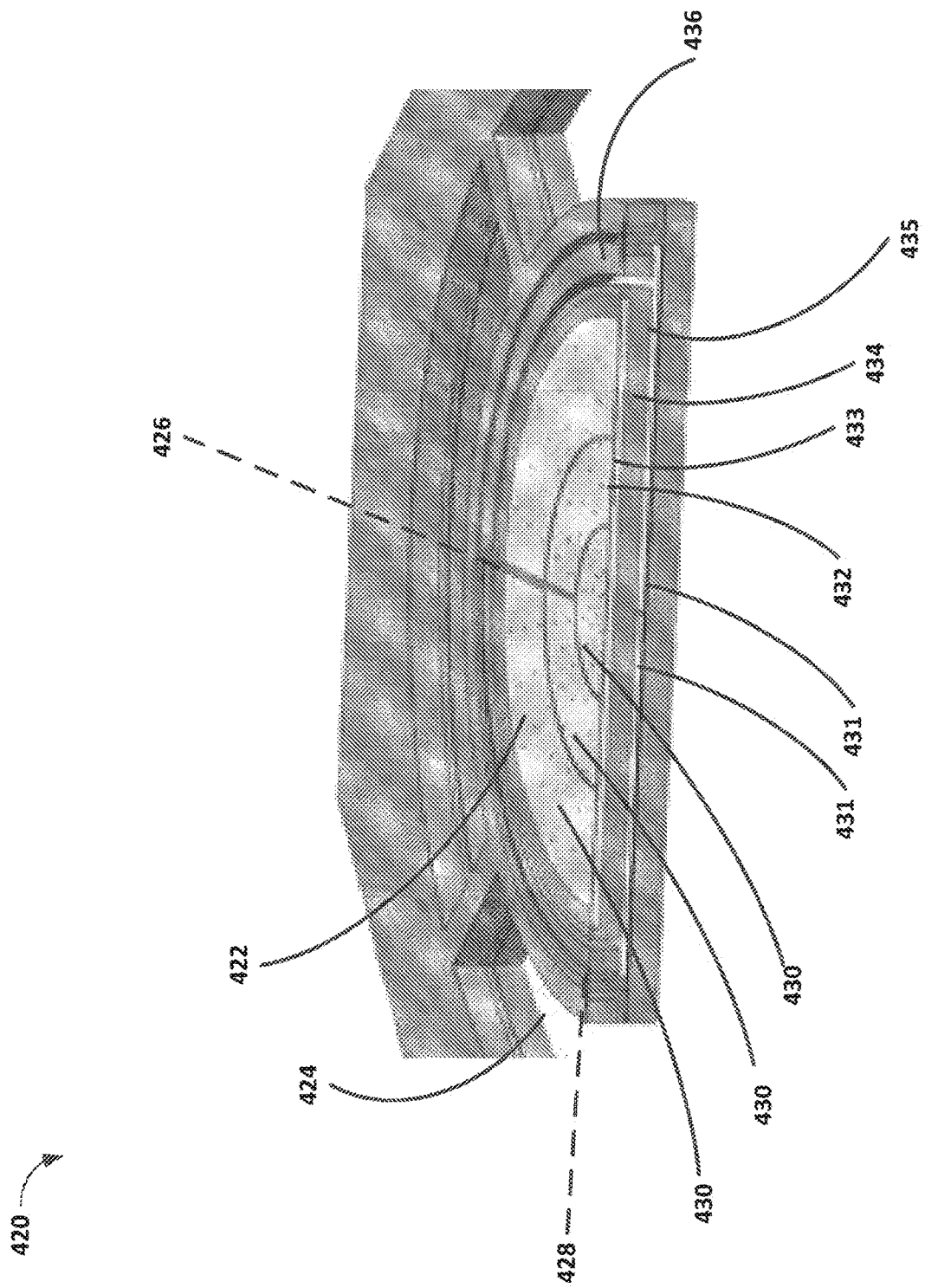
FIG. 19 illustrates a cross-sectional view of the scanner shown in FIG. 18.

The SU-8 membrane mirror is integrated on a silicon gimbal platform, with parallel plate electrodes beneath the silicon to control tip and tilt (x-y scanning). Electrodes on the surface of the membrane control focus and aberration. FIGS. 18 and 19 show the structure. The micromachining process will be quite similar to our earlier 3D MEMS mirrors, but the membrane is spin-cast SU-8 rather than vapor-deposited silicon nitride. The new mirrors will meet the specifications shown in Table 2.

TABLE 2

MEMS x-y-z scanner metrics x-scan: ±2° mechanical, resonant near 2 kHz
y-scan: ±2° mechanical, non-resonant (1st torsional mode > 200 Hz)
x-y scan rate up to 8 fps (500 lines per frame bi-directional)
Mirror aperture size: 3.5 mm-overall gimbal dimension 4.0 mm
membrane stroke: >16 μm (achieves 150 μm focus range in tissue with NA = 0.75)

TABLE 2-continued

MEMS x-y-z scanner metrics focus control electrodes: 3
correction of primary spherical up to 1 μm p-v residual (unwanted) aberration: <100 nm
z-scan (focus) maximum frequency: >5 kHz As illustrated in FIG. 18, one embodiment of reflective variable focus lens 420 includes reflective surface 422 and annular aperture 424. In this embodiment, reflective surface 422 provides both focus and scanning functionality for reflective variable focus lens 420, as further described in FIG. 19. Annular aperture 424 allows beams to pass through reflective variable focus lens 420, in this embodiment.

FIG. 19 illustrates an embodiment of reflective variable focus lens 420 in greater detail. In this example embodiment, reflective surface 422 and annular aperture 424 are shown as in FIG. 18. Reflective surface 422 is comprised of suspended membrane 432 and control electrodes 430, in this example embodiment. Control electrodes 430 control focus and spherical aberration (adjustments to curvature of reflective surface 422) of suspended membrane 432 in this embodiment. Membrane air gap 433 permits suspended membrane 432 to adjust focus and spherical aberration in response to control electrodes 430. Gimbal control electrodes 431 control tip and tilt of gimbal plate 434 about x-axis 428 and y-axis 426. Gimbal air gap 435 provides space to adjust gimbal plate 434 in response to control signals from gimbal control electrodes 431. Gimbal ring 436 rotates about x-axis 428, but permits rotation of gimbal plate 434 about both x-axis 428 and y-axis 426, within tolerance of gimbal air gap 435 in this embodiment. Focus and scanning control in this embodiment are achieved by suspended membrane 432 changing focus and spherical shape in response to control electrodes 430 while tip and tilt are controlled by gimbal plate 434 in response to gimbal control electrodes 431.

To test the performance of the new mirrors, the x-y scanning range and speed is measured using a reflected laser beam and position-sensitive detector. To measure focus and aberration control, a phase-shift interferometer is used to provide 2D surface mapping of the focus control membranes. Dynamic deformation is measured using a stroboscopic illumination source, both static and dynamic surface shape changes can therefore be quantified. Measured mechanical behavior will be compared to finite element models. Our comprehensive characterization plan will clearly demonstrate whether or not the mirrors as developed will meet the demanding requirements of the iLSM optical system.

FIG. 16 illustrates an embodiment of an integrated laser scanning microscope 500 integrating camera 120, as previously described, and reflective variable focus lens 420, as previously described. In this example embodiment of integrated laser scanning microscope 500, within housing 580 beams 570 pass through doublet 560 and are then reflected by reflecting lens 540 to reflective variable focus lens 550 providing microscopic view of a small area. Camera 510 provides wide-field view illuminated by light-emitting diodes 520 through hyperhemisphere lens 530. In this example embodiment of integrated laser scanning microscope 5X), both microscopic view and wide-field view can be achieved in a single device without degradation of either view.

FIG. 17 illustrates another embodiment of the integrated laser scanning microscope 600 integrating camera 120, as previously described, and reflective variable focus lens 420, as previously described. In this example embodiment, camera 608 is not positioned on hyperhemisphere lens 610 but rather beside hyperhemisphere lens 610. As previously described, right-angle reflecting prism 604 redirects light through hyperhemisphere lens 610 to provide dermoscopy in this embodiment. Light-emitting diodes 602 illuminate the target image which is captured by camera 608. In this example embodiment of integrated laser scanning microscope 600, beams 618 are reflected by reflecting lenses 612 to reflective variable focus lens 606 providing microscopic view of a small area. In this example embodiment, the illumination laser beam is delivered by a single mode polarization maintaining fiber. Passage of the laser light and the reflected light through quarter wave plate 614 converts the reflected light to a crossed polarization state. Wollaston prism 616 redirects the crossed-polarization reflected light toward a larger core detection optical fiber, where the core size can be chosen according to the desired pinhole size for confocal detection. The use of polarization maintaining fiber, quarter wave plates, Wollaston prisms, and large core fibers are all known to those skilled in the art. In this example embodiment of integrated laser scanning microscope 600, both microscopic reflectance confocal view and wide-field view can be achieved in a single device without degradation of either view.

Various features and advantages of the invention are set forth in the following claims.

What is claimed is:

1. A device for viewing a target, the device comprising:
a housing;
an objective lens positioned within the housing, the objective lens including a first lens group including at least a first lens and a second lens group including at least a second lens, the first lens positioned closer to the target than the second lens; and
a camera positioned within the objective lens between the first lens and the second lens, the camera configured to provide images of the target located near a focal point of the objective lens,
wherein the arrangement of the first lens, the second lens, and the camera provides for simultaneous capture of a high numerical aperture microscopic image and a low numerical aperture wide-field image.

2. The device of claim 1, wherein a first portion of the first lens provides for the high numerical aperture microscopic image and a second portion of the first lens provides for the low numerical aperture wide-field image.

3. The device of claim 2, wherein the first portion is an outer portion of the first lens and wherein the second portion is a central portion of the first lens.

4. The device of claim 3, wherein the first portion accounts for 75% of the diameter of the first lens and the second portion accounts for 25% of the diameter of the first lens.

5. The device of claim 2, wherein the first portion of the first lens provides for a numerical aperture of 0.7 or greater and wherein the second portion of the first lens provides for a numerical aperture of less than 0.7.

6. The device of claim 5, wherein the first portion of the first lens provides for a field of view equal to or less than 1 mm and wherein the second portion of the first lens provides for a field of view greater than 1 mm.

7. The device of claim 1, wherein the arrangement of the first lens, the second lens, and the camera provides for simultaneous imaging of a surface of the target and imaging of a sub-surface cellular structure of the target, wherein the imaging of the surface of the target is executed via the low numerical aperture wide-field imaging, and wherein the imaging of the subsurface cellular structure of the target is executed via the high numerical aperture microscopic imaging.

8. The device of claim 7, wherein the imaging of the sub-surface cellular structure of the target is non-invasive.

9. The device of claim 1, wherein the first lens group includes at least one selected from the group consisting of: a hyperhemisphere lens, an aplanatic hemisphere lens, and an aplanatic hyperhemisphere lens.

10. The device of claim 9, wherein the second lens group includes a lens having a numerical aperture between 0.2 and 0.5.

11. The device of claim 1, wherein the camera is configured to provide wide-field imaging of a surface morphology of the target, and further comprising a beam scanner and/or focusing device configured to provide three-dimensional sub-surface imaging of a portion of the target.

12. The device of claim 11, wherein the beam scanner is positioned between the camera and the second lens group.

13. The device of claim 1, further comprising a reflecting element adjacent to the first lens, and configured to redirect light reflected from the target to the camera.

14. The device of claim 1, wherein the low numerical aperture wide-field image shows the surface of the target and the high numerical aperture microscopic image shows a sub-surface cellular structure of the target.

* * * * *